US012586190B2

(12) United States Patent
Ramirez et al.

(10) Patent No.: US 12,586,190 B2
(45) Date of Patent: **\*Mar. 24, 2026**

(54) SYSTEM AND METHOD OF CLASSIFICATION OF BIOLOGICAL PARTICLES

(71) Applicant: Iris International, Inc., Chatsworth, CA (US)

(72) Inventors: Carlos Ramirez, Miami, FL (US); Steven Cadavid, Delray Beach, FL (US); Jindan Zhou, Palmetto Bay, FL (US)

(73) Assignee: Iris International, Inc., Chatsworth, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/544,074

(22) Filed: Dec. 18, 2023

(65) Prior Publication Data

US 2024/0212149 A1      Jun. 27, 2024

Related U.S. Application Data

(63) Continuation of application No. 17/850,234, filed on Jun. 27, 2022, now Pat. No. 11,900,598, which is a
(Continued)

(51) Int. Cl.
*G06T 7/00* (2017.01)
*G06T 7/33* (2017.01)
(Continued)

(52) U.S. Cl.
CPC ............ *G06T 7/0012* (2013.01); *G06T 7/001* (2013.01); *G06T 7/33* (2017.01); *G06T 7/41* (2017.01);
(Continued)

(58) Field of Classification Search
CPC ......... G06T 7/001; G06T 7/0012; G06T 7/33; G06T 7/41; G06T 2207/10056;
(Continued)

(56) References Cited

U.S. PATENT DOCUMENTS

| | | | |
|---|---|---|---|
| 4,612,614 A | 9/1986 | Deindoerfer et al. | |
| 7,236,623 B2 | 6/2007 | Chapoulaud et al. | |
(Continued)

FOREIGN PATENT DOCUMENTS

| | | |
|---|---|---|
| CN | 102663406 A | 9/2012 |
| CN | 103745210 A | 4/2014 |
(Continued)

OTHER PUBLICATIONS

"U.S. Appl. No. 16/324,795, Advisory Action mailed Jan. 27, 2021", 5 pgs.
(Continued)

*Primary Examiner* — Katrina R Fujita
(74) *Attorney, Agent, or Firm* — Schwegman Lundberg Woessner, P.A

(57) ABSTRACT

A method and system for classification of cells and particles in a biological sample using an automated image-based feature extraction and classification architecture. A method operates by applying a mask or series of masks to an image, extracting features from the unmasked portions of the image based on the content and location of colored pixels, selecting a subset of the extracted features, and mapping the subset of the extracted features into a classifier architecture. In a majority of cases, the first level model architecture provides an accurate identification of the cell or particle. In a minority of cases, the classification of the cell or particle requires a second level step requiring the use of numerical or categorical values from the first level in combination with a second level model.

20 Claims, 13 Drawing Sheets

Related U.S. Application Data continuation of application No. 16/324,795, filed as application No. PCT/US2017/047993 on Aug. 22, 2017, now Pat. No. 11,403,751.

(60) Provisional application No. 62/377,851, filed on Aug. 22, 2016.

(51) Int. Cl.

| | |
|---|---|
| *G06T 7/41* | (2017.01) |
| *G16B 5/00* | (2019.01) |
| *G16B 40/10* | (2019.01) |
| *G16B 50/30* | (2019.01) |
| *G16H 10/40* | (2018.01) |
| *G16H 30/40* | (2018.01) |

(52) U.S. Cl.

CPC .............. *G16B 5/00* (2019.02); *G16B 40/10* (2019.02); *G16B 50/30* (2019.02); *G16H 10/40* (2018.01); *G16H 30/40* (2018.01)

(58) Field of Classification Search

CPC ....................... G06T 2207/30024; G16B 5/00; G16B 40/10; G16B 50/30; G16H 10/40; G16H 30/40

See application file for complete search history.

(56) References Cited

U.S. PATENT DOCUMENTS

| | | | |
|---|---|---|---|
| 8,879,813 | B1 | 11/2014 | Solanki et al. |
| 11,403,751 | B2 | 8/2022 | Ramirez et al. |
| 2004/0126008 | A1 | 7/2004 | Chapoulaud |
| 2005/0251347 | A1 | 11/2005 | Perona |
| 2015/0110348 | A1 | 4/2015 | Solanki et al. |
| 2018/0025211 | A1 | 1/2018 | Aragaki |
| 2019/0228527 | A1 | 7/2019 | Ramirez et al. |
| 2022/0335609 | A1 | 10/2022 | Ramirez et al. |

FOREIGN PATENT DOCUMENTS

| | | | |
|---|---|---|---|
| CN | 105408746 | A | 3/2016 |
| CN | 109952614 | A | 6/2019 |
| CN | 109952614 | B | 11/2023 |
| EP | 3500964 | A1 | 6/2019 |
| HK | 40010506 | A | 7/2020 |
| JP | 2001512824 | A | 8/2001 |
| JP | 2004505233 | A | 2/2004 |
| JP | 2007309804 | A | 11/2007 |
| JP | 2015137857 | A | 7/2015 |
| JP | 2019529882 | A | 10/2019 |
| JP | 7104691 | B2 | 7/2022 |
| JP | 2022137166 | A | 9/2022 |
| WO | WO-2018039216 | A1 | 3/2018 |

OTHER PUBLICATIONS

"U.S. Appl. No. 16/324,795, Advisory Action mailed Dec. 15, 2021", 6 pgs.

"U.S. Appl. No. 16/324,795, Corrected Notice of Allowability mailed Apr. 28, 2022", 3 pgs.

"U.S. Appl. No. 16/324,795, Corrected Notice of Allowability mailed Jun. 30, 2022", 3 pgs.

"U.S. Appl. No. 16/324,795, Examiner Interview Summary mailed Nov. 23, 2021", 2 pgs.

"U.S. Appl. No. 16/324,795, Final Office Action mailed Oct. 7, 2021", 26 pgs.

"U.S. Appl. No. 16/324,795, Final Office Action mailed Nov. 18, 2020", 21 pgs.

"U.S. Appl. No. 16/324,795, Non Final Office Action mailed May 4, 2021", 23 pgs.

"U.S. Appl. No. 16/324,795, Non Final Office Action mailed Jul. 6, 2020", 17 pgs.

"U.S. Appl. No. 16/324,795, Notice of Allowance mailed Mar. 24, 2022", 8 pgs.

"U.S. Appl. No. 16/324,795, Preliminary Amendment filed Feb. 11, 2019", 7 pgs.

"U.S. Appl. No. 16/324,795, Response filed Jan. 15, 2021 to Final Office Action mailed Nov. 18, 2020", 9 pgs.

"U.S. Appl. No. 16/324,795, Response filed Aug. 4, 2021 to Non Final Office Action mailed May 4, 2021", 11 pgs.

"U.S. Appl. No. 16/324,795, Response filed Oct. 5, 2020 to Non Final Office Action mailed Jul. 6, 2020", 10 pgs.

"U.S. Appl. No. 16/324,795, Response filed Dec. 1, 2021 to Final Office Action mailed Oct. 7, 2021", 8 pgs.

"U.S. Appl. No. 17/850,234, Non Final Office Action mailed Apr. 21, 2023", 26 pgs.

"U.S. Appl. No. 17/850,234, Notice of Allowance mailed Oct. 6, 2023", 8 pgs.

"U.S. Appl. No. 17/850,234, Preliminary Amendment filed Jun. 28, 2022", 8 pgs.

"U.S. Appl. No. 17/850,234, Response filed Jul. 18, 2023 to Non Final Office Action mailed Apr. 21, 2023", 7 pgs.

"U.S. Appl. No. 17/850,234, Supplemental Preliminary Amendment filed Jul. 7, 2022", 6 pgs.

"Brazilian Application Serial No. 1120190031448, Office Action mailed Jan. 28, 2023", w/ English Translation, 5 pgs.

"Brazilian Application Serial No. 1120190031448, Voluntary Amendment filed Aug. 24, 2020", w/ Current English Claims, 68 pgs.

"Chinese Application Serial No. 201780051805.0, Office Action mailed Jul. 25, 2023", W/English Translation, 7 pgs.

"Chinese Application Serial No. 201780051805.0, Office Action mailed Nov. 18, 2022", w/ English Translation, 11 pgs.

"Chinese Application Serial No. 201780051805.0, Response filed Mar. 31, 2023 to Office Action imailed Nov. 18, 2022", w/ English Claims, 15 pgs.

"Chinese Application Serial No. 201780051805.0, Response filed Oct. 7, 2023 to Office Action mailed Jul. 25, 2023", w/ english claims, 16 pgs.

"European Application Serial No. 17761164.7, Communication Pursuant to Article 94(3) EPC mailed Jun. 4, 2021", 8 pgs.

"European Application Serial No. 17761164.7, Response Filed Sep. 23, 2021 to Communication Pursuant to Article 94(3) EPC mailed Jun. 4, 2021", W/ Claims, 10 pgs.

"European Application Serial No. 17761164.7, Response to Communication Pursuant to Rules 161 and 162 filed Dec. 19, 2019", 14 pgs.

"Indian Application Serial No. 201947010445, First Examination Report mailed Aug. 3, 2021", with English translation, 6 pages.

"Indian Application Serial No. 201947010445, Voluntary Amendment filed Aug. 26, 2020", English claims, the agent only provided US with the amended claims (marked and clean), so I kept the e-receipt in the PDF just in case. I dont think they filed an explanation of the amendments., 12 pgs.

"International Application Serial No. PCT/US2017/047993, International Preliminary Report on Patentability mailed Mar. 7, 2019", 10 pgs.

"International Application Serial No. PCT/US2017/047993, International Search Report mailed Nov. 16, 2017", 3 pgs.

"International Application Serial No. PCT/US2017/047993, Written Opinion mailed Nov. 16, 2017", 8 pgs.

"Japanese Application Serial No. 2019-510405, Notification of Reasons for Refusal mailed Aug. 27, 2021", with English translation, 4 pages.

"Japanese Application Serial No. 2019-510405, Response Filed Jan. 21, 2022 to Notification of Reasons for Refusal mailed Aug. 27, 2021", with English claims, 12 pages.

"Japanese Application Serial No. 2019-510405, Voluntary Amendment filed Aug. 20, 2020", w/ English claims, 11 pgs.

"Japanese Application Serial No. 2022-110246, Notification of Reasons for Refusal mailed Sep. 1, 2023", w/ English Translation, 5 pgs.

"Japanese Application Serial No. 2022-110246, Response filed Sep. 26, 2023 to Notification of Reasons for Refusal mailed Sep. 1, 2023".

(56) References Cited

OTHER PUBLICATIONS

"Korean Application Serial No. 10-2019-7005157, Notice of Preliminary Rejection mailed Feb. 25, 2022", with English translation, 15 pages.
"Korean Application Serial No. 10-2019-7005157, Response filed Apr. 25, 2022 to Notice of Preliminary Rejection mailed Feb. 25, 2022", w/ English Claims, 17 pgs.
"Korean Application Serial No. 10-2019-7005157, Voluntary Amendment filed Aug. 12, 2020", w/ English claims, 16 pgs.

100

115 ANALYZER 145   140

MEMORY
INSTRUCTIONS

110 COMPUTING DEVICE

190 NETWORK COMPONENTS

160 DISPLAY

130 BUS

I/O CONTROLLER

165 MONITOR

120 PROCESSOR

STORAGE

150

170 KEYBOARD

180

185 CLASSIFIER ARCHITECTURE

187 FIRST LEVEL MODEL

189 SECOND LEVEL MODEL

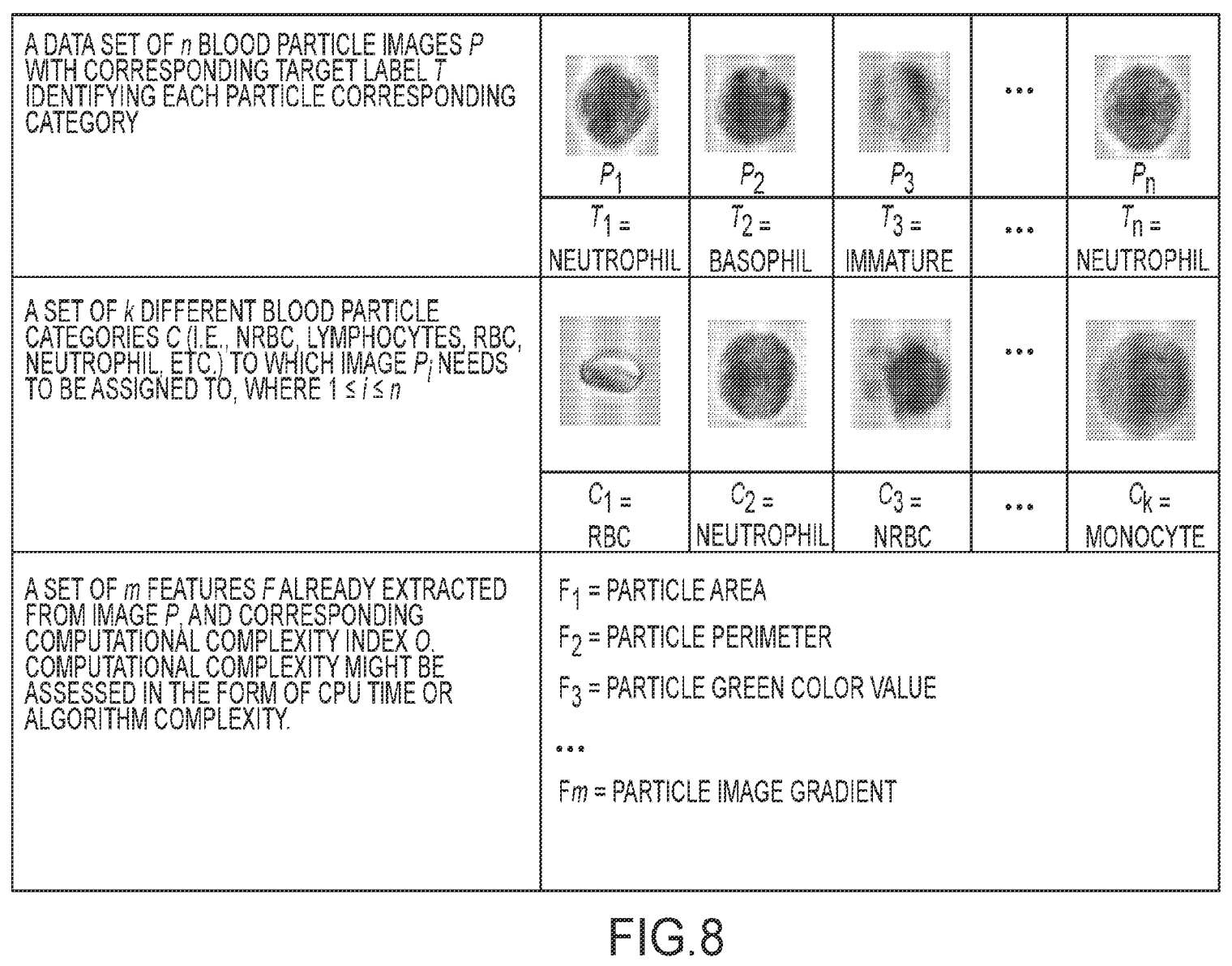

A DATA SET OF $n$ BLOOD PARTICLE IMAGES $P$ WITH CORRESPONDING TARGET LABEL $T$ IDENTIFYING EACH PARTICLE CORRESPONDING CATEGORY

A SET OF $k$ DIFFERENT BLOOD PARTICLE CATEGORIES $C$ (I.E., NRBC, LYMPHOCYTES, RBC, NEUTROPHIL, ETC.) TO WHICH IMAGE $P_i$ NEEDS TO BE ASSIGNED TO, WHERE $1 \leq i \leq n$ A SET OF $m$ FEATURES $F$ ALREADY EXTRACTED FROM IMAGE $P$ AND CORRESPONDING COMPUTATIONAL COMPLEXITY INDEX $O$. COMPUTATIONAL COMPLEXITY MIGHT BE ASSESSED IN THE FORM OF CPU TIME OR ALGORITHM COMPLEXITY.

$P_1$   $P_2$   $P_3$   ...   $P_n$ $T_1 =$ NEUTROPHIL   $T_2 =$ BASOPHIL   $T_3 =$ IMMATURE   ...   $T_n =$ NEUTROPHIL $C_1 =$ RBC   $C_2 =$ NEUTROPHIL   $C_3 =$ NRBC   ...   $C_k =$ MONOCYTE $F_1 =$ PARTICLE AREA $F_2 =$ PARTICLE PERIMETER $F_3 =$ PARTICLE GREEN COLOR VALUE

...

$Fm =$ PARTICLE IMAGE GRADIENT

FIG.8

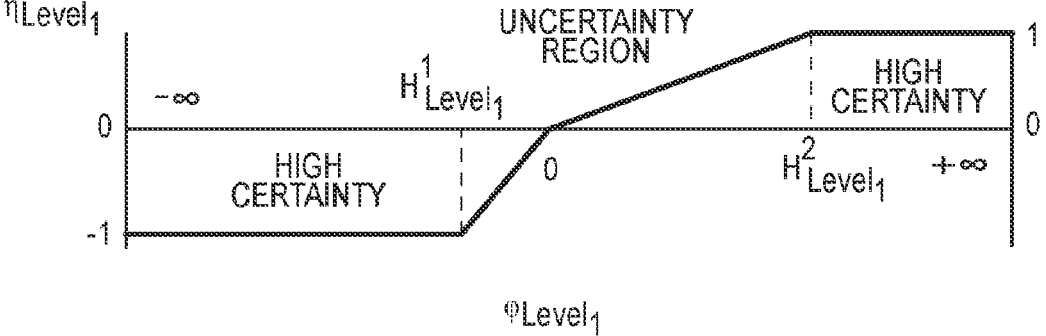
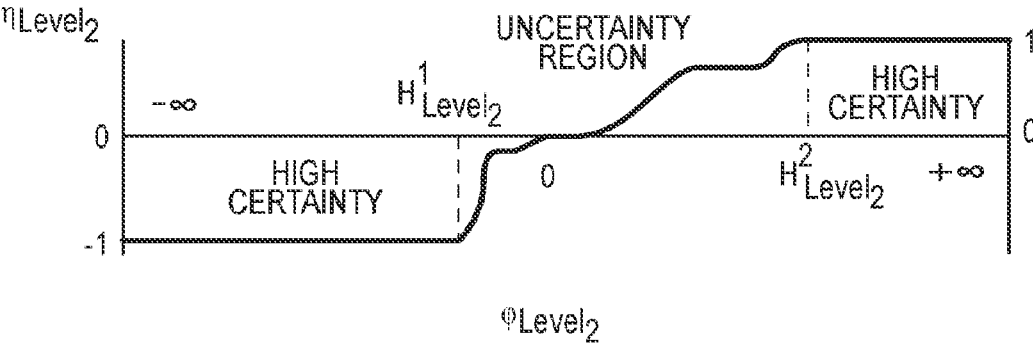
FIG.12

SYSTEM AND METHOD OF CLASSIFICATION OF BIOLOGICAL PARTICLES

BACKGROUND

The identification and enumeration of biological particles, including cells and particles is useful in a host of research and clinical applications, including the detection of hematological conditions.

Automated biological particle recognition is a task that requires complex operations to be executed in a time sensitive manner, oftentimes on hardware with limited computational resources. It is therefore important that each phase in the system be efficient. Automated biological particle recognition, particularly for blood cells, has conventionally been done using techniques which require heavy preprocessing. This results in a necessary compromise between computational efficiency and descriptive power. Furthermore, analysis and troubleshooting of conventional systems can be cumbersome if not impossible due to the large number of factors required for such complex operations.

Accordingly, there remains a need for improved methods to decrease computational requirements while increasing the efficiency and accuracy of automated biological particle classification. Embodiments of the present disclosure address this and other problems.

SUMMARY

This disclosure relates to a system containing an automated image-based feature extraction and classification architecture which is suitable for real-time classification of biological particles, including cells and other particles, in a biological sample. This system may be used as a medical diagnostic tool and may enhance the identification and quantification of cells and/or particles. The disclosed image-based classification system includes four major steps, image acquisition, feature extraction, feature selection, and the determination of a cell or particle's classification using a cascade classifier architecture. To analyze the cells and/or particles contained within a biological sample, images of the cells or particles may first be collected or acquired. Using these images, the system may then extract particular numerical or categorical values or characteristics known as "features" from the individual images. The system may then use hierarchical or cascaded classification architecture in analysis of the extracted features.

According to various embodiments, the cascade classifier architecture used in the determination step may include a two-level analysis. If the outcome of the first level analysis is inconclusive, the second level analysis may be performed on the selected ones of the extracted features of the biological sample (e.g. a blood sample).

In an exemplary architecture, a select set of the extracted features of the biological sample may be compared to a select set of features extracted from cells or particles with known characteristics. In a majority of cases, comparison ("first level model") provides an accurate identification of the cell or particle. In a minority of cases, the classification of the cell or particle requires a further step (a "second level model") to classify the cell or the particle. This step may include the use of numerical or categorical values from the first level model in combination with a second level model. This two-level architecture allows the system to accurately assign each image into a class or category, either after the first or second level.

The blood particle feature selection and image classifier architecture systems and methods discussed herein can provide various benefits and advantages when compared to other traditional approaches. For example, embodiments of the present invention provide systems and methods where feature extraction computational complexity can be kept to a minimum value. In some cases, complex and costly feature computation can be postponed until a cell event reaches a particular classifier within the architecture that requires the specific feature. In many cases the majority of the features will not need to be computed. Feature extraction can be a costly stage of any automated classification system. The architecture systems and methods disclosed herein introduce a simple yet powerful approach to balance complexity and performance. Moreover, the the cascade architecture of the classifier system can be modular, scalable, and simple to post-analyze. The output of the system can be easily traced back to individual classifiers. Individual classifiers can be easily retrained or upgraded while maintaining untouched the rest of the architecture In contrast, many traditional approaches are composed of a single classifier with a large number of features which makes analysis and troubleshooting of the architecture cumbersome if not impossible. Exemplary systems and methods disclosed herein can provide an order of processing in the cascade architecture that is defined in the feature selection stage which uses separability measurements among all categories in the training data. The separability metrics can be used to decide which category is the easiest to process at the beginning of the classification workflow. The complex separability cases among categories can be left to the end of the cascade According to exemplary system and method embodiments, the feature of transfer functions between the low level complexity (Level 1) and high level complexity (Level 2) within a classifier can allow a smooth transition between both levels. This can reduce variability in the system response when similar images with small changes in feature values are processed due to the fact that there are no hard thresholds but rather a continuous transition between the two levels.

In one aspect, provided is a method of determining a classification of a particle in a biological sample, the method including acquiring an image of the particle, receiving, at a processor system, the image of the particle, and executing, using the processor system, computer executable code stored on a non-transitory computer readable medium, the computer executable code comprising instructions on the processor system. In some instances, when executed on the processor system, the instructions cause the processor system to perform an extraction routine that may include extracting a plurality of features from the image based on content and location of pixels of the image. In some instances, the extracting includes applying a first mask to the image, acquiring a first set of pixels from the image based on applying the first mask, and determining the plurality of features from the first set of pixels In some instances, the mapping includes performing a mapping routine that includes mapping the subset of the extracted features into a classifier architecture. In some instances, the mapping includes using a first level model to compare the subset of the extracted features to a previously stored data set and identifying a preliminary classification based on the comparison of the subset of the extracted features to the previously stored data set. In some instances, the mapping includes calculating a probability value that the preliminary classification is correct using the first level model, and may also include determining the classification based on the preliminary classification when the probability value is at or above a threshold value.

In one aspect, provided is a method of determining a classification of a particle in a biological sample, the method including acquiring an image of the particle, extracting a plurality of features from the image based on content and location of pixels of the image, selecting a subset of the extracted features, and mapping the subset of the extracted features into a cascade classifier architecture, calculating a probability value that the preliminary classification is correct using the first level model, and determining the classification based on the preliminary classification when the probability value is at or above a threshold value. In some instances, the extracting includes applying a first mask to the image, acquiring a first set of pixels from the image based on applying the first mask, and determining the plurality of features from the first set of pixels. In some instances, the mapping includes using a first level model to compare the subset of the extracted features to a previously stored data set and identifying a preliminary classification based on the comparison of the subset of the extracted features to the previously stored data set. In some instances, the mapping includes calculating a probability value that the preliminary classification is correct using the first level model, and may also include determining the classification based on the preliminary classification when the probability value is at or above a threshold value.

In some instances, the method of extracting includes applying a second mask to the image to acquire a second set of pixels. In some instances, the first mask and the second mask may be circular or ring-shaped. In some instances, the application of different masks reveals different pixels. In some instances, the first mask and the second mask may be applied in a predetermined order.

In some instances, the method of extracting includes clustering the first set of pixels into a group.

In some instances, the method of extracting includes creating a color palette from the clustered group of pixels.

In some instances, the method of extracting includes determining a label for the image based in part on the color palette.

In some instances, the method of extracting includes normalizing the image to a mask size.

In some instances, the method of extracting includes normalizing the first mask to a unit magnitude.

In some instances, the method of extracting includes using a chosen color space, including red-green-blue (RGB) hue-saturation-value (HSV), hue-saturation-lightness (HSL), or hue-saturation-brightness (HSB).

In some instances, the selected subset of the extracted features comprises training features, validation features, or testing features. In some instances, the subset of the extracted features is mapped into a cascade classifier architecture.

In some instances, the first level model is a machine learning model.

In some instances, the method of mapping includes using a second level model to determine the cell or particle classification when the probability value is below the threshold value.

In some instances, the second level model is a machine learning model.

In some instances, the particle may be a neutrophil, a lymphocyte, a monocyte, an eosinophil, a basophil, an immature white blood cell, a reticulocyte, a nucleated red blood cell, an erythrocyte, an epithelial cell, a bacterium, a yeast, or a parasite.

In another aspect, provided is a method of determining a classification of a particle in a biological sample, the method including a second level model. In some instances, the second level model includes receiving the probability value at the second level model, creating a sorted list of values according to a classification performance in relation to a cell or particle category, combining the probability value and the sorted list to create a second level probability value, and using the probability value determined at the first level model and the probability value determined at the second level model to determine the cell or particle classification.

In another aspect, provided is a system for determining a classification of a particle in a biological sample, the system including a processor and a computer-readable storage medium coupled to the processor, the computer readable storage medium comprising code executable by the processor for implementing a method, the method including acquiring an image of the particle, extracting a plurality of features from the image based on content and location of pixels of the image, selecting a subset of the extracted features, and mapping the subset of the extracted features into a cascade classifier architecture. In some instances, the extracting includes applying a first mask to the image, acquiring a first set of pixels from the image based on applying the first mask, and determining the plurality of features from the first set of pixels. In some instances, the mapping includes using a first level model to compare the subset of the extracted features to a previously stored data set, identifying a preliminary classification based on the comparison of the subset of the extracted features to the previously stored data set, calculating a probability value that the preliminary classification is correct using the first level model, and determining the classification based on the preliminary classification when the probability value is at or above a threshold value. In some cases, the computer readable storage medium includes code executable by the processor for implementing any of the methods disclosed herein. In some instances, the system uses a digital microscope camera. Embodiments of the present invention also encompass a non-transitory computer-readable storage medium including program instructions executable by one or more processors that, when executed, cause the one or more processors to perform operations, the operations including any of the methods disclosed herein.

In another aspect, provided is a method of determining a classification of a particle in a biological sample by mapping a subset of extracted features into a cascade classifier architecture, the mapping including using a first level machine learning model to compare the subset of extracted features to a previously stored data set, wherein the extracted features may be extracted from images, calculating a probability value using the first level machine learning model, comparing the probability value to a predetermined comparison table, determining a cell classification if the probability value is at or above a threshold value, using a second level machine learning model if the probability value is below the threshold value, creating an ascending sorted list of values according to their classification performance in relation to a cell or particle category using the second level machine learning model, combining the probability value and the sorted list of values to create a second level score, using the second level score to determine a cell classification.

The foregoing, together with other features and embodiments will become more apparent upon referring to the following specification, claims, and accompanying drawings.

BRIEF DESCRIPTION OF THE DRAWINGS

FIG. 8 illustrates aspects of blood particle images, blood particle categories, and extracted features according to some embodiments of the invention.

FIG. 12 illustrates exemplary transition functions between Level 1 and Level 2 classifier outputs according to embodiments of the present invention.

DETAILED DESCRIPTION

Figure 1A:
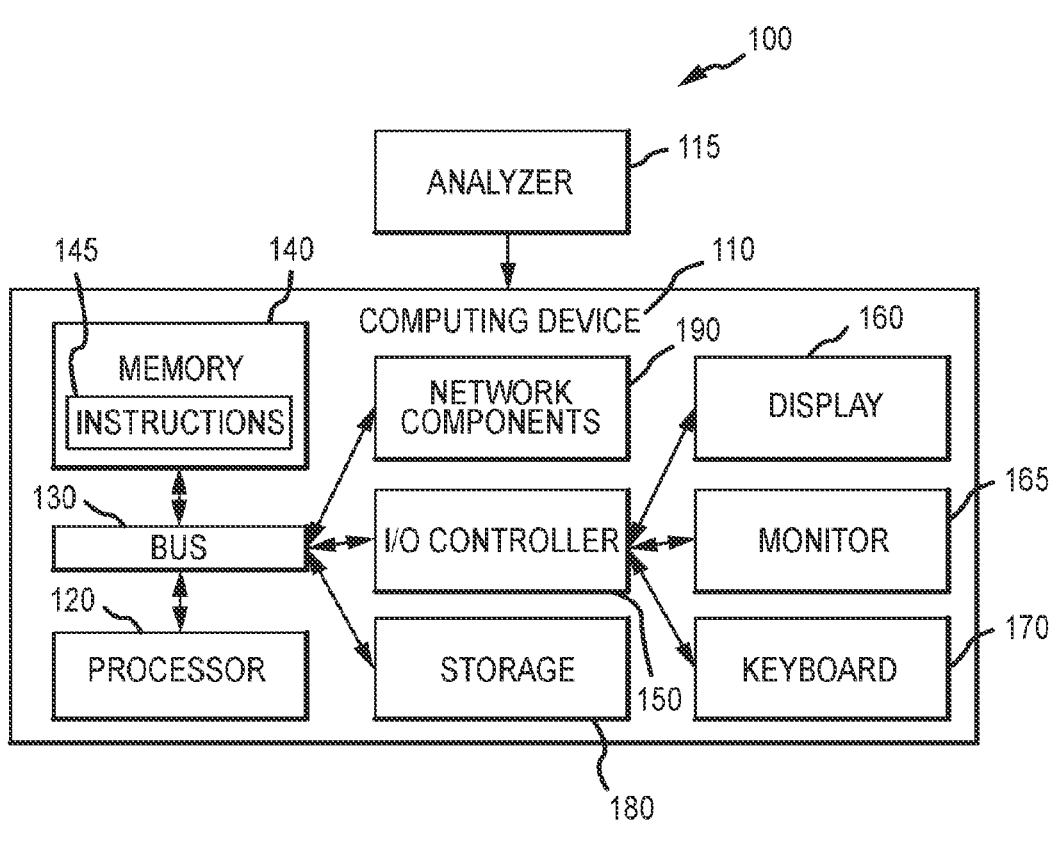
FIGS. 1A and 1B illustrate block diagrams of an example system and architecture that may be used to implement embodiments disclosed herein.

In the following description, for the purposes of explanation, specific details are set forth in order to provide a thorough understanding of embodiments of the invention. However, it will be apparent that various embodiments may be practiced without these specific details. For example, circuits, systems, algorithms, structures, techniques, networks, processes, and other components may be shown as components in block diagram form in order not to obscure the embodiments in unnecessary detail.

It is to be understood that embodiments of the invention may include more or fewer than the components shown individually in a diagram. The figures and description are not intended to be restrictive.

Also, it is noted that individual embodiments may be described as a process which is depicted as a flowchart, a flow diagram, a data flow diagram, a structure diagram, or a block diagram. Although a flowchart may describe the operations as a sequential process, many of the operations may be performed in parallel or concurrently In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

This disclosure relates to a system containing an automated image-based feature extraction and classification architecture which is suitable for real-time classification of cells and/or particles in a biological sample.

Automated particle classification systems may be used to analyze biological samples to determine the composition and/or number of one or more types of cells and/or particles contained in the samples. These systems commonly include hematology analyzers and flow cytometers. For example, the analysis of the cellular populations in peripheral blood includes the ability to detect and enumerate the five major subtypes of white blood cells (WBC), which include neutrophils, lymphocytes, monocytes, eosinophils and basophils. For example, the main red blood cells (RBC) in peripheral blood are reticulocytes and nucleated red blood cells. These cellular populations have differing shapes and functions, and the number and presence of these populations in a sample may differ according to pathological conditions, cell maturity and other factors. Cell classification systems may differentiate cells of various types by collecting and analyzing signals produced when the cells pass through a small aperture or measurement region that is monitored by one or more instruments. Advantageous aspects of an automated cell classification system include the capability to identify a plurality of types of cells, based on their architecture, and also to identify artifacts resulting from the cellular processing or image acquisition process (e.g. images that depict old or damaged cells and images that are out of focus).

Hematology

Blood cell analysis is one of the most commonly performed medical tests for providing an overview of a patient's health status. A blood sample can be drawn from a patient's body and stored in a test tube containing an anticoagulant to prevent clotting. A whole blood sample normally comprises three major classes of blood cells including red blood cells (erythrocytes), white blood cells (leukocytes) and platelets (thrombocytes). Each class can be further divided into subclasses of members. For example, five major types or subclasses of white blood cells (WBCs) have different shapes and functions. White blood cells may include neutrophils, lymphocytes, monocytes, eosinophils, and basophils. There are also subclasses of the red blood cell types. The appearances of particles in a sample may differ according to pathological conditions, cell maturity and other causes. Red blood cell subclasses may include reticulocytes and nucleated red blood cells.

In some embodiments, the particle is selected from at least one of neutrophil, lymphocyte, monocyte, eosinophil, basophil, platelet, reticulocyte, nucleated red blood cell (RBC), blast, promyelocyte, myelocyte, metamyelocyte, red blood cell (RBC), platelet, cell, bacteria, particulate matter, cell clump, or cellular fragment or component.

Unless expressly indicated otherwise, references to "particle" or "particles" made in this disclosure will be understood to encompass any discrete or formed object dispersed in a fluid. As used herein, "particle" can include all measurable and detectable (e.g., by image and/or other measurable parameters) components in biological fluids. The particles are of any material, any shape and any size. In certain embodiments, particles can comprise cells. Examples of particles include but are not limited to cells, including blood cells, fetal cells, epithelialis, stem cells, tumor cells, or bacteria, parasites, or fragments of any of the foregoing or other fragments in a biological fluid. Blood cells may be any blood cell, including any normal or abnormal, mature or immature cells which potentially exist in a biological fluid, for example, red blood cells (RBCs), white blood cells (WBCs), platelets (PLTs) and other cells. The members also include immature or abnormal cells. Immature WBCs may include metamyelocytes, myelocytes, pro-myelocytes and blasts. In addition to mature RBCs, members of RBCs may include nucleated RBCs (NRBCs) and reticulocytes. PLTs may include "giant" PLTs and PLT clumps. Throughout the specification, the images are described as being an image of a cell or a particle. Though referred to as a cell in many cases, the images may be of any particle.

Exemplary particles can include formed elements in biological fluid samples, including for example, spherical and non-spherical particles. In certain embodiments, the particles can comprise non-spherical components. In some embodiments, platelets, reticulocytes, nucleated RBCs, and WBCs, including neutrophils, lymphocytes, monocytes, eosinophils, basophils, and immature WBCs including blasts, promyelocytes, myelocytes, or metamyelocytes are counted and analyzed as particles.

Urinalysis

Exemplary urine particles can include urine sediment particles. Exemplary urine sediment particles can include erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, *trichomonas*, cell clumps, and cell fragments. Exemplary cells can include red blood cells, white blood cells, and epithelials. Exemplary casts can include acellular pigment casts, unclassified cast (e.g. granular casts). Exemplary acellular casts can include, for example, waxy casts, broad casts, fatty casts, and crystal casts. Exemplary cellular casts can include, for example, RBC casts, WBC casts, and cellular casts. Exemplary crystals can include, for example, calcium oxalate, triple phosphate, calcium phosphate, uric acid, calcium carbonate, leucine, cystine, tyrosine, and amorphous crystals. Exemplary non-squamous epithelial cells can include, for example, renal epithelials and transitional epithelials. Exemplary yeast can include, for example, budding yeast and yeast with pseudohyphae. Exemplary urinary sediment particle can also include RBC clumps, fat, oval fat bodies, and *trichomonas*.

The system may be useful, for example, in characterizing particles in biological fluids, such as detecting and quantifying erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, *trichomonas*, cell clumps, and cell fragments, categorization and subcategorization, counting and analysis.

The assignment of cell and/or particle images into different classes or categories may be a complex computational task. While some analysis and comparisons can be done through an automated system, not all images of cells and/or particles are sufficiently clear or are similar enough to images of cells and/or particles with known characteristics and/or properties for automation to work properly or effectively. The extracted features may have different degrees of computational complexity. In many cases, cells and/or particles may be classified using a low number or complexity of extracted features, for example by using color-based features. Typically, color-based features are a fast computational task, whereas texture and shape features are a slow computational task and could impose a constraint for real-time classification. The real-time analysis constraint relates to the fact that the processing of a stream of particles may need to conclude within a certain expected time in order for the acquisition system to meet predefined throughput requirements. However, under certain disease conditions or system related changes (stain, focus, cell aging, others) additional features with a higher complexity, and therefore features requiring greater computational task, might be needed to correctly identify the appropriate cell and/or particle category. Using features of high complexity for all particles requiring identification is not always feasible due to time and/or computing constraints. Embodiments herein provide a classification architecture that may be suitable for real-time classification of cells and/or particles, for example blood cells and/or particles.

More specifically, embodiments may provide a system which may be used as a medical diagnostic tool and may enhance the identification and quantification of cells and/or particles. The disclosed image-based classification system includes four major steps: image acquisition, feature extraction, feature selection, and the determination of a cell or particle's classification using a cascade classifier architecture. To analyze the cells and/or particles contained within the biological sample, images of the cells and/or particles may first be collected or acquired. Using these images, the system may then extract particular numerical or categorical values or characteristics known as "features" from the individual images. The system may then use hierarchical or cascaded classification architecture in analysis of the extracted features. According to various embodiments, the cascade classifier architecture used in the determination step may include a two-level analysis. If the outcome of the first level model is inconclusive, the second level analysis may be performed on the selected ones of the extracted features of the biological sample (e.g. a blood sample).

In an exemplary architecture, a select set of the extracted features of the biological sample may be compared to a select set of features extracted from cells or particles with known characteristics. In a majority of cases, comparison ("first level model") provides an accurate identification of the cell or particle. In a minority of cases, the classification of the cell or particle requires a further step (a "second level model") to classify the cell or the particle. This step may include the use of numerical or categorical values from the first level model in combination with a second level model. This two-level architecture allows the system to accurately assign each image into a class or category, either after the first or second level.

Image Acquisition

In some embodiments, the system may include an analyzer for collecting or acquiring images of the particles. In some embodiments, the analyzer may be a visual analyzer. In one aspect, this disclosure relates to an automated particle imaging system in which a liquid sample containing particles of interest is caused to flow through a flow cell having a viewport through which a high optical resolution imaging device captures an image. In some aspects, the high optical resolution imaging device comprises a camera such as a digital camera. In one aspect the high optical resolution imaging device comprises an objective lens. Exemplary image acquisition techniques which facilitate the capturing of images with a high level of resolution have been described in other applications and are incorporated in their entirety by reference, including patent application Ser. No.

14/216,811 entitled ANALYSIS OF PARTICLES IN FLUID SAMPLES, filed Mar. 17, 2014, and patent application Ser. No. 14/775,448 entitled HEMATOLOGY SYSTEMS AND METHODS, filed Sep. 11, 2015. Additional aspects of image acquisition may include, but are not limited, to preprocessing of the images to remove noise and/or compensate for changes in illumination.

FIG. 1A illustrates a block diagram of an example system 100 usable for performing automated cell or particle recognition according to embodiments of the present invention. The system 100 may include various components, including a computing device 110, and analyzer 115. The analyzer 115 may collect images of biological particles and/or cells through, for example, a bodily fluid system that captures images of bodily fluid cells as described in detail in patent application Ser. No. 14/775,448 entitled HEMATOLOGY SYSTEMS AND METHODS, filed Sep. 11, 2015. The system 100 may perform feature extraction, feature selection, and classification via cascade classifier architecture and may use information determined in this analysis to classify a cell and/or particle. Images for classification may be stored in the storage 180 and/or received by the computer from an external device or database. For example, the analyzer 115 may collect images and store them in the storage 180. Reference images may be collected through analyzer 115 and/or through other capture methods for comparison and may be stored in the storage 180. The system 100 may include a computing device 110, which may be, for example, a desktop computer, laptop computer, tablet, e-reader, smart phone or mobile device, smart watch, personal data assistant (PDA), or other electronic device. The computing device 110 may be in a cloud computing environment. The computing device 110 may be utilized by a user. The computing device 110 may include a processor 120 interfaced with other hardware via a bus 130. The system 100 preferably includes one or more software programs or instructions 145 stored on a memory 140 of the computing device 110. The instructions 145 may be operable to perform a cascade classifier architecture, such as the cascade classifier architecture 185 illustrated in FIG. 1B. The software programs may be stored in a machine-readable memory 140 of the system 100. The term "memory" is intended herein to include various types of memory, including an installation medium, e.g., a CD-ROM, or floppy disks, a computer system memory such as DRAM, SRAM, EDO RAM, Rambus RAM, etc. . . . or a non-volatile memory such as a magnetic medium, e.g., a hard drive, or optical storage. The memory 140 may comprise other types of memory as well, or combinations thereof. The memory 140 may embody program components (e.g., instructions 145 and/or the cascade classifier architecture 185) that configure operation of the computing device 110. In some examples, the computing device 110 may include input/output ("I/O)") interface components 150 (e.g., for interfacing with a display 160, monitor 165, or keyboard 170, or mouse) and storage 180. Storage 180 may store sample images from the camera input as well as reference images for analysis. In some embodiments, the reference images may be used as training data for a neural network implementation of the cascade classifier architecture. The storage 180 may include any suitable database including, for example, a Microsoft® SQL Server® database, an Oracle® database, or a Microsoft® Excel® spreadsheet.

The computing device 110 may further include network components 190. Network components 190 may represent one or more of any components that facilitate a network connection. In some examples, the network components 190 may facilitate a wireless connection and include wireless interfaces such as IEEE 802.11, Bluetooth, or radio interfaces for accessing cellular telephone networks (e.g., a transceiver/antenna for accessing CDMA, GSM, UMTS, or other mobile communications network). In other examples, the network components 190 may be wired and may include interfaces such as Ethernet, USB, or IEEE 1394.

Additionally, the storage medium 180 may be located in a first computer in which the programs may be executed, or may be located in a second different computer which connects to the first computer over a network 190. In the instance of a network 190, a second computer may provide the program instructions 145 to the first computer for execution. Although FIG. 1A depicts a single computing device 110 with a single processor 120, the system 100 may include any number of computing devices 110 and any number of processors 120. For example, multiple computing devices 110 or multiple processors 120 may be distributed over a wired or wireless network (e.g., a Wide Area Network, Local Area Network, or the Internet). The multiple computing devices 110 or multiple processors 120 may perform any of the steps of the present disclosure individually or in coordination with one another.

Figure 1B:
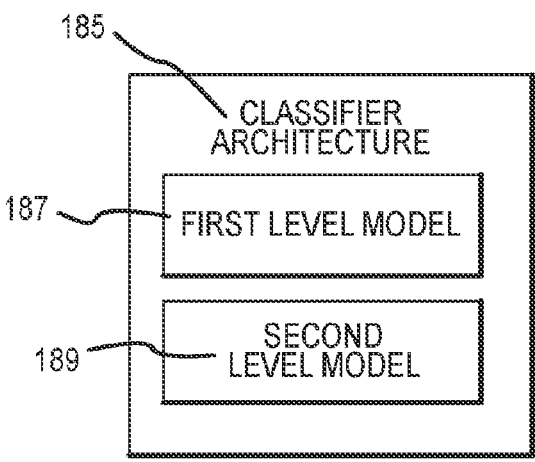

FIG. 1B illustrates an exemplary cascade classifier architecture 185. The cascade classifier architecture may contain two level models and may be capable of performing two-level analysis. In an example, a first level model 187 may provide an accurate identification of the cell or particle or the cascade classifier architecture 185 may further use a second level model 189 to provide an accurate identification of the cell or particle. The second level model 189 may include the use of numerical or categorical values from the first level model 187 in combination with the second level model 189. When the output of the first level model 187 is unclear or indefinite, the second level model 189 may be used. The images for analysis in the cascade classifier architecture 185 may come from the storage 180 or directly from the analyzer 115 may be input to the first level model 187. If necessary, the same may be input to the second level model. The output of the first level model 187 may be input to the second level model 189.

Figure 2:
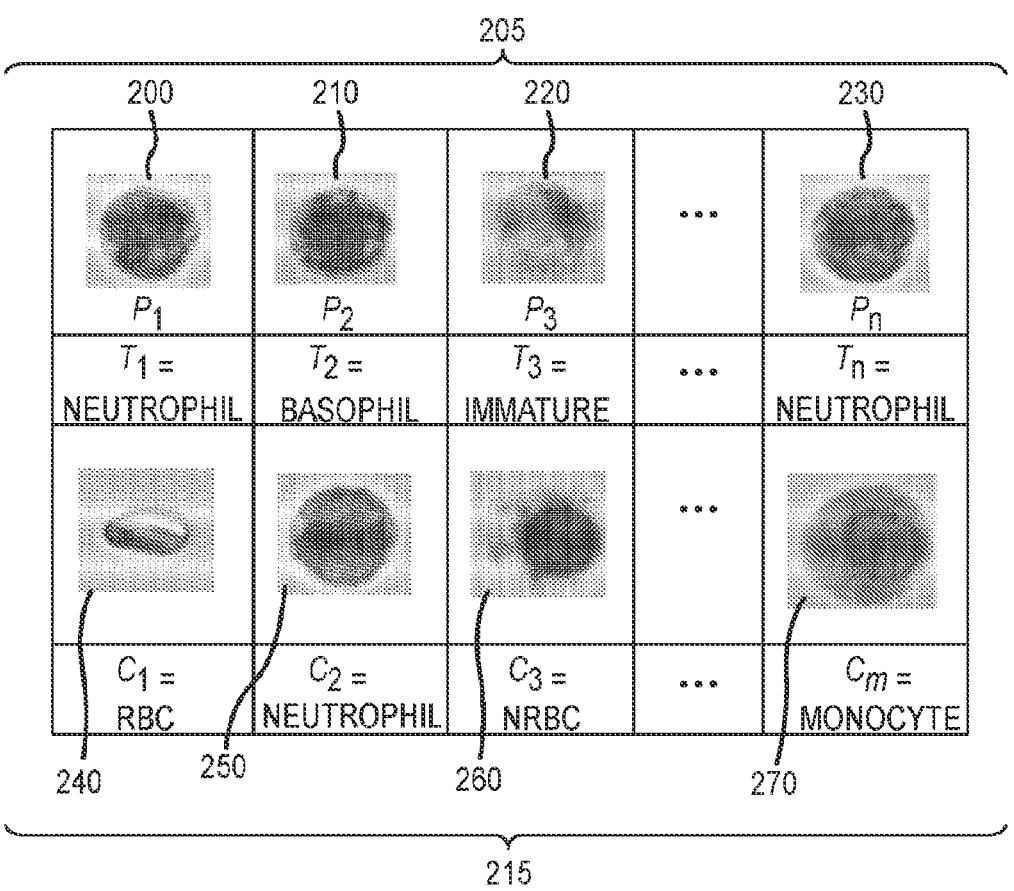
FIG. 2 illustrates exemplary blood cell images according to some embodiments of the invention.

FIG. 2 illustrates sample blood cell images 200-270 that may be used in systems and methods disclosed herein. As used herein, n refers to a data set of blood particle images P illustrated in the first row 205 with corresponding target label T'identifying each particle to a corresponding category. As used herein, m refers to different blood particle categories C (i.e., NRBC, Lymphocytes, RBC, Neutrophil, etc.) illustrated in the second row 215 to which image $P_i$ may be assigned to, where $1 \le i \le n$. As used herein, the letter "k" is used to refer to a single category belonging to the set of "m" available categories.

Feature Extraction

Feature extraction is intended to reduce the amount of data needed to analyze and discriminate among a set of categories. This process may interpret or summarize a large amount of information as a value that may later be used to make a determination. Extracted features may include numerical values that correlate with a particular characteristic of the data. For example, in an image, instead of using all colors as input to a cascade classifier architecture, a mean and standard deviation along all colors may be extracted as a feature. In image processing, feature extraction may have varying degrees of computational complexity. Highly complex extraction procedures may involve segmentation of the image to isolate a region of interest and prevent lengthy computational operations in that area while still extracting meaningful information. Simple extraction procedures may involve shape features, including but not limited to area, perimeter, and circularity. Extraction procedures may involve gradient profiles to detect edges. Extraction profiles may involve color intensity, histogram color mean, mode, standard deviation, or color thresholding. Extraction procedures may mean histogram differences or ratios between channel red and channel green, between channel red and channel blue, and/or between channel green and channel blue.

In some instances, an image may have thousands of pieces of information (e.g. data points), which may be extracted as features. In some instances, images may be composed of three colored images: one red, one green, and one blue image.

In the system 100 for determining a cell or particle classification in a biological sample, as described herein, the features of the images may be extracted and stored in a computing device's memory 140, and so the original images need not be stored long-term in the analyzer 115. Thus, when the determination of cell or particle type takes place, the images may be represented by the extracted features alone. According to the feature extraction method described herein, a color space quantization method may be used to extract a set of unique color features from an image. This method may perform a majority of the computational calculations not in real-time, also known as in an off-line stage. In an off-line stage, the images may be stored and analyzed at a later time than when the images are obtained. This is advantageous over other feature extraction methods because off-line processing uses no computational task energy resulting in faster online processing times. Because off-line processing is not heavily constrained by time, the computation and extraction of computationally expensive complex mathematical transformations may result in better discriminative features. In some instances, feature extraction may take place in part or in whole off-line. In some instances, feature extraction may take place in part or in whole online.

The feature extraction method may create a "color feature signature" based on the location and value of the colors in the image. The color feature signature may include a histogram obtained by accumulating the number of pixels belonging to each of the palette colors. To extract the color feature signature for each biological particle, a palette of colors corresponding to the most representative colors in selected regions of the image for different biological particle types may be constructed. In some instances, the feature extraction may include clustering a set of pixels into a group. Each pixel may be assigned to the closest color in the palette. The resulting color feature signature may be a histogram with an amplitude value for each color in the palette.

Figure 3:
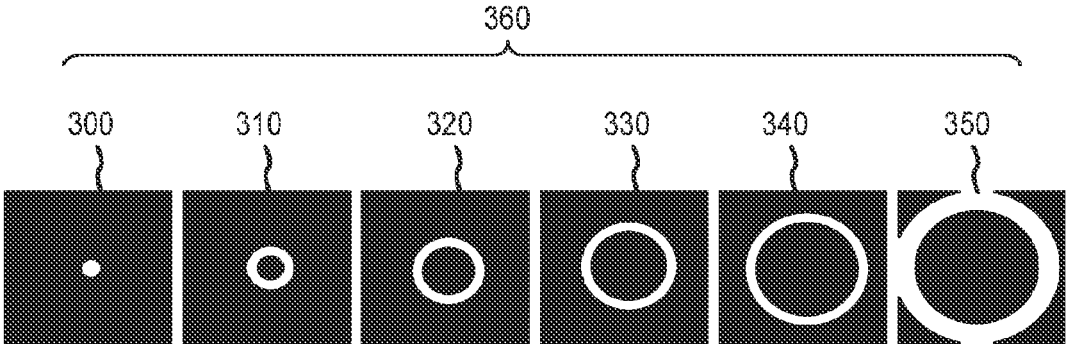
FIG. 3 illustrates an exemplary set of binary concentric ring masks according w some embodiments of the invention.

In one embodiment, to incorporate both location and color information, the color space quantization approach may create a set of R binary masks composed of individual concentric rings. FIG. 3 shows an example of R 360. When the concentric ring masks 300-350 are used, the resulting image plane projection of the cells will generally be circular in shape. The ring masks 300-350 may be isotropic and thus feature signatures derived using the rings may be rotation invariant. In an imaging system, scale invariance may be inherent when the distance to the cell and/or particle imaged is fixed. The centroid of each ring mask 100-150 may be dynamic and determined by features in the image such as intensity or entropy. In the simplest case, the location may be fixed and defined as the center of the image 100. This enables translation invariance of the feature signature.

The width and number r of ring masks 300-350 in R 360 may be heuristically chosen based on final classification performance. Each ring mask 300-350 may be used to filter pixels from the original cell image. The masks in a set 360 may be applied in any order. Once an order of masks is chosen for a set 360, the same predetermined order may be used and applied for image analysis. The masks in a set 360 do not necessarily reveal adjacent areas of the image, but may reveal adjacent areas of the image. To apply the ring mask 300-350 to the cell image, the cell image may be first normalized to the size of the ring mask 300-350. Pixels falling into each ring mask 300-350 may then be extracted and analyzed in a chosen color space (i.e., red-green-blue ("RGB") hue-saturation-value ("HSV"), hue-saturation-lightness ("HSL"), etc.).

In one embodiment, the RGB color space may be chosen as the analysis space of the masked cell image. In such an embodiment, the process to extract the color palette given a set of ring masks 300-350 begins with the normalization of all cell images $P_i$ to the size of the ring masks $R_l$ to enable the application of the masks to the cell images. In this normalization, $P^{C_i}$ may denote the set of all normalized cell images $P_i$ with corresponding target label $T_i$ in the training set equal to blood cell category $C_j$, $1{\leq}j{\leq}m$.

For each blood cell category $C_j$, to avoid a bias by the variable count of cell images in each $P^{C_j}$, a random subset of cell images may be selected in $P^{C_j}$, $\gamma^{C_j} {\subseteq} P^{C_j}$, $\gamma^{C_j}{=}\{\gamma_t{}^{C_j}\}_{t=1}{}^{n_\gamma}$, $n_\gamma{=}\min_{1{\leq}j{\leq}m}|P^{C_j}|$, where the size of the subset, $n_\gamma$, is equal to the minimum number of cell images across all $P^{C_j}$.

For each ring mask $R_l$, $1{\leq}l{\leq}r$
Mask all cell images in $\gamma^{C_j}$ with ring mask $R_l$
Form a set of RGB pixels $V^l$ from the retained pixels in the masked cell images.
For each ring mask $R_l$, $1{\leq}l{\leq}r$
For each set of pixels $V^l$ in $R_l$
Cluster $V^l$ into h groups resulting in a set of h cluster centers $VC_l{}^1$, $1{\leq}j{\leq}h$;
Create ring color palette $PLT_l{=}\{VC_1{}^l, vC_2{}^l, \ldots, VC_h{}^l\}$;
Create the final palette $$PLT = \{PLT_1, PLT_2, \ldots, PLT_r\}$$

Figure 4:
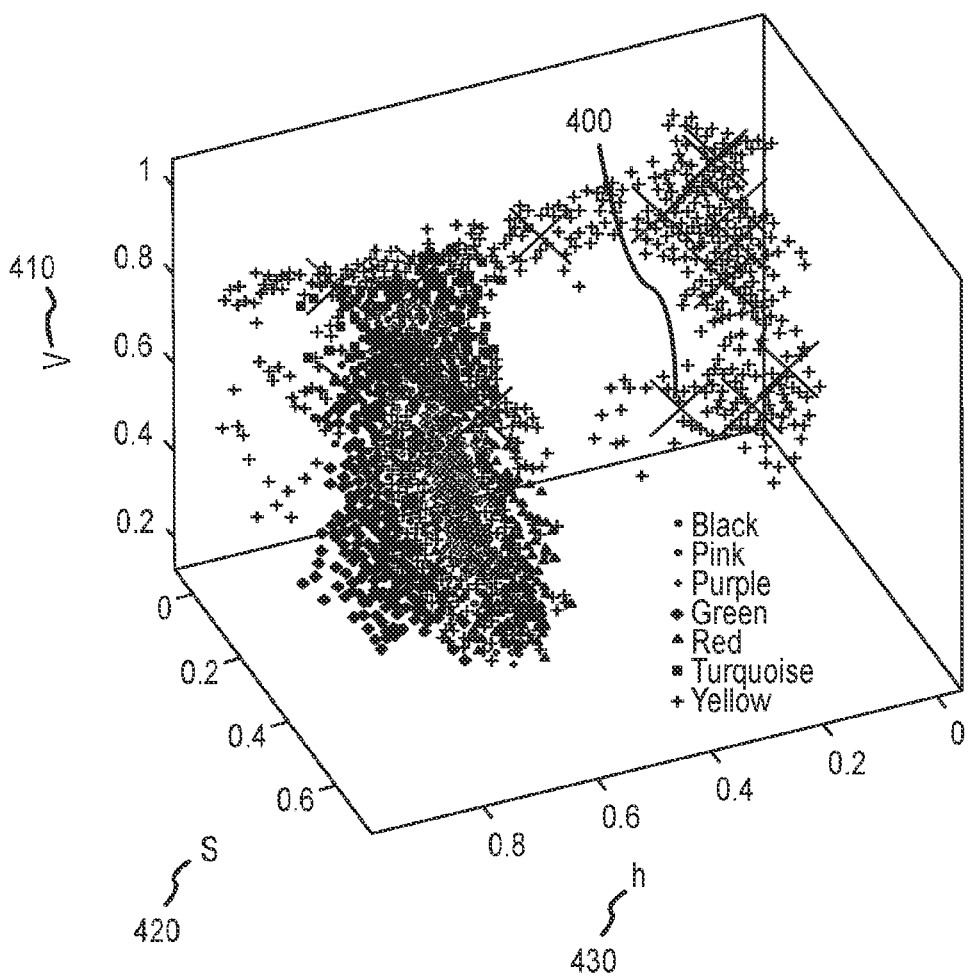
FIG. 4 illustrates an exemplary clustering for a single binary ring mask according to some embodiments of the invention.

FIG. 4 shows an example of the clustering process for a given ring mask in the HSV color space, where the X 400 in the chart represents the center of the clusters and each color is associated to pixels belonging to a cell category, the s-axis 410 represents the Saturation component, the h-axis 420 represents the Hue component, and the v-axis 430 represents the Value or brightness. The pixels belonging to a given category may further be identified by using other visual cues, such as color. Each cell category may be represented by a different number of images in the training set (e.g. reference images). To reduce the bias towards a particular cell type with a greater representation in the training set, the color samples used for clustering may be sampled from an equal number of training set images across the cell categories. In this example, the different cell categories (identified by the different colors) occupy different location in the color space from the other cell categories, and furthermore each cell category has a different distribution within the chart.

Figure 5:
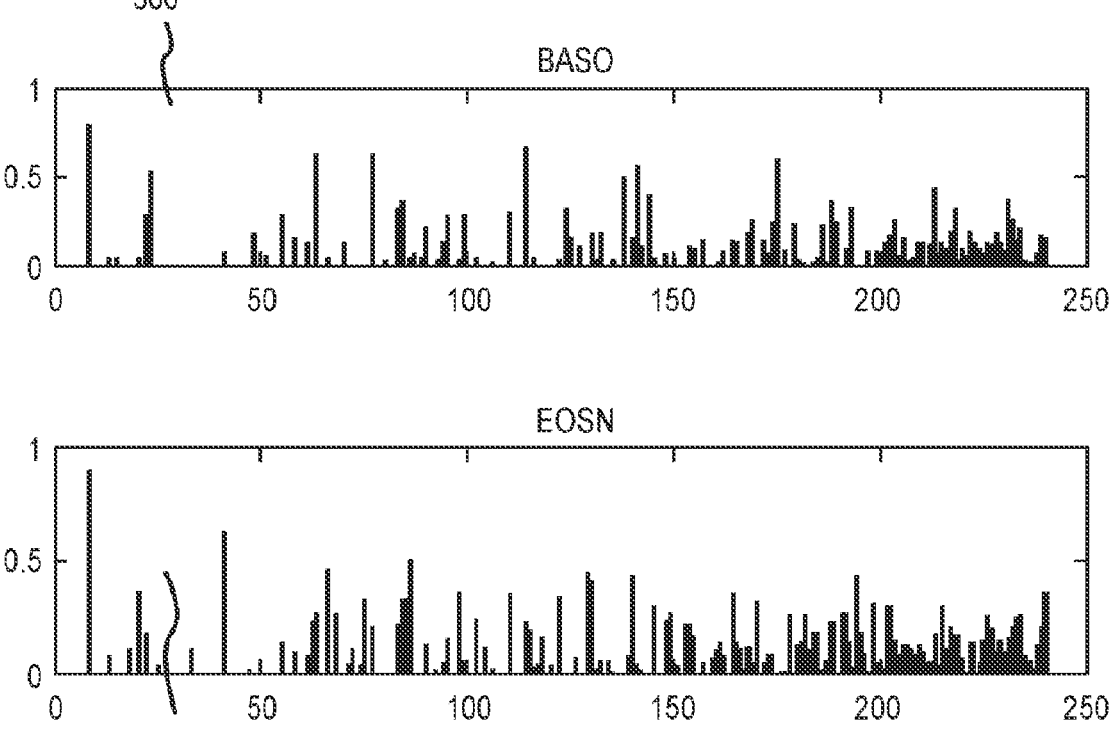
FIG. 5 illustrates exemplary feature histograms for the white blood cell types Basophils and Eosinophils according to some embodiments of the invention.

A training set or training features may be evaluated against the color palette to create, for each image, a corresponding color histogram. The training data or the reference images may be a previously stored data set. FIG. 5 shows an example of the feature histogram for the white blood cell types Basophils 500 and Eosinophils 510. The data may be split into intervals called bins, which may be represented in vertical rectangles on a histogram. Each bin in the histogram which corresponds to each set of cluster centers $VC_j^l$ may become an input feature for the cascade classifier architecture 185 (e.g. input feature 610 illustrated in FIG. 6A). During the online (also known as real-time processing) feature extraction process, the color quantization may be accelerated by storing the mapping between the color space and generated palette using look up tables or other indexing methods (e.g. k-dimensional trees). In some instances, as the ring in the mask 300-350 becomes larger in diameter, a greater number of pixels may be retained and contribute to the corresponding histogram. Consequently, the ring masks 300-350 may yield histograms with different sample counts. Using such histograms for classification may introduce a bias towards the ring masks 300-350 with a larger diameter because the sample counts for those ring masks 300-350 may be greater. To address this issue, each histogram vector may be normalized to unit magnitude.

Feature Normalization

Examples of feature vector normalization schemes include L2-norm, L1-norm, L2-norm followed by clipping, and L1-norm followed by square root and etc. In out implementation, L2-norm scheme is selected for histogram vector normalization. Let h be the non-normalized histogram vector, the normalized histogram vector is defined as:

$$f = \frac{h}{\|h\|_2}, \text{ where } \|h\|_2 = \sqrt{h_1^2 + h_2^2 ... h_n^2}$$

is the, L2-norm of vector h.

The normalization of images to a common mask size may discard the relative size information between the images. The image width may be appended to the feature vector as a final feature to preserve the cell or particle size information. The features extracted may be augmented with additional morphological features such as gradient, entropy, etc., to complement the extracted information available in the color space.

Feature Selection

Feature selection, which is also known as subset selection or variable selection, is a method used in machine learning to select a subset of features from all of the features available in a dataset. It is utilized in machine learning prior to applying a learning algorithm because it is computationally infeasible to use all available features in a dataset. Feature selection also may minimize problems of estimation and over fitting when a dataset contains limited data samples containing a large number of features. For example, a cell image may contain thousands of features, which may not all be good for analysis. The selection of particular features may depend on the specifications of the system. The selection of particular features may depend on the speed requirements for extraction within a particular system. Extracted features may include features used for training, validation, and/or testing (i.e. "training features, validation features, or testing features").

Classifier Architecture

Figure 6A:
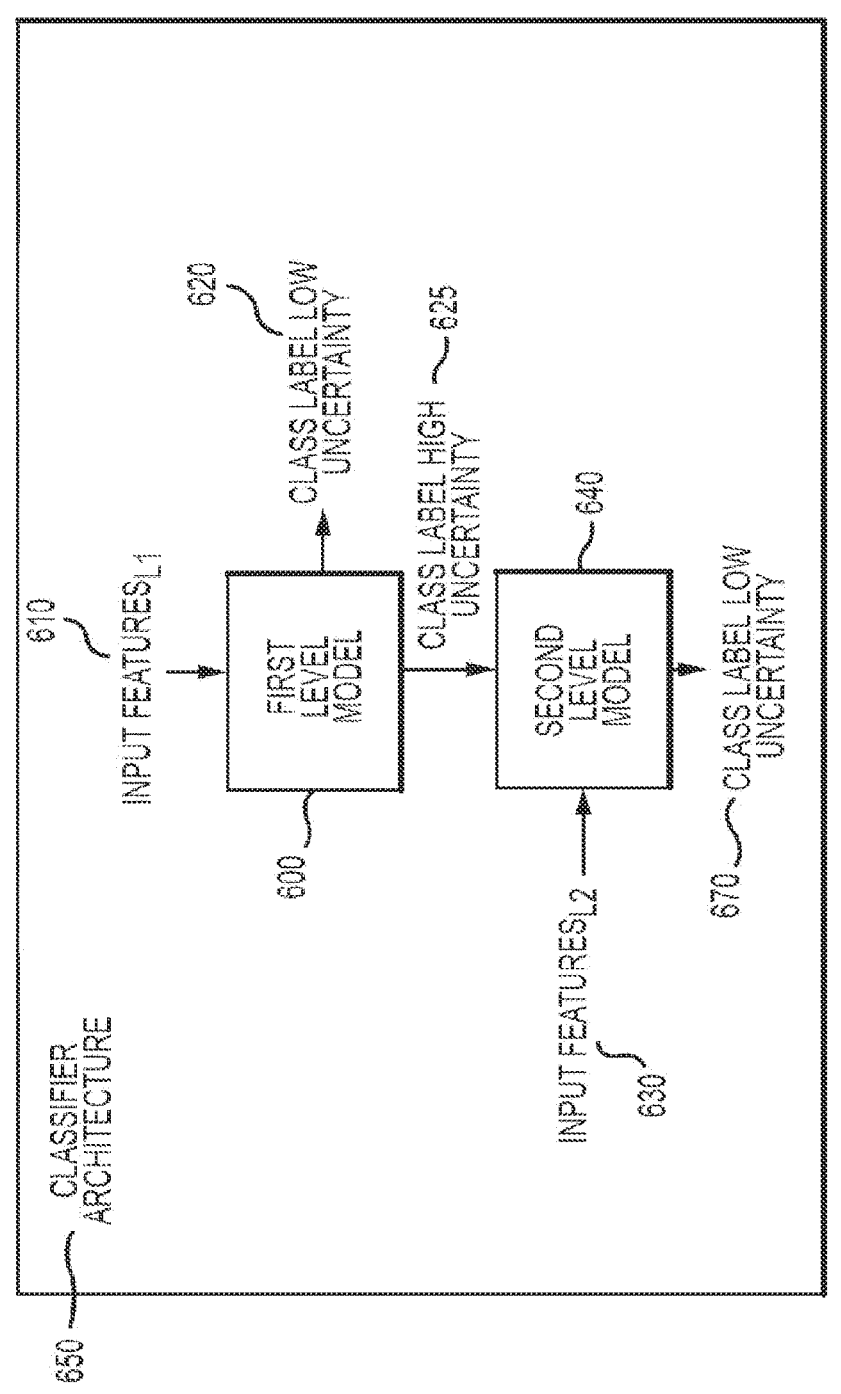
FIGS. 6A and 6B Illustrate exemplary architecture models of the cell classification system according to some embodiments of the invention.

A classifier architecture is a set of rules governing the transitions between classifier states. In some instances, a classifier may include a cascade of evaluation or processing stages, such as a first level model and a second level model. In an exemplary embodiment, the first level model may generate an opinion in the form of a level of confidence between zero and one. If the level of confidence is at or above a certain threshold, a decision may be made regarding the identity of the imaged particle or cell. In an exemplary embodiment, if the level of confidence is below a certain threshold, the information may be sent to the second level model. The second level model may use a more complex level of features than the first level model, including in some instances a random forest of decision trees, in combination with the level of confidence from the first level model, to make a decision regarding the identity of the imaged particle or cell. An exemplary cascade classifier architecture 650 including a first level model 600 and a second level model 640 is illustrated in FIG. 6A.

In a classifier architecture (e.g. the exemplary cascade classifier architecture 650), a subset of the features extracted may be selected using appropriate separability measures and a final data set may be constructed. The data may be consolidated in a table where each row corresponds to a particular cell (and therefore to a cell image) and the Features columns correspond to the unique features associated with the corresponding cell category, as shown in exemplary TABLE 1. In TABLE 1, the Category column serves the purpose of defining the "true" label or class for each cell.

TABLE 1

| Cell | Category | Feature 1 | Feature 2 | ... | Feature s |
|------|----------|-----------|-----------|-----|-----------|
| $P_1$ | $T_1$ (Neutrophil) | 3.4 | −4.3 | ... | 23.3 |
| $P_2$ | $T_2$ (Basophil) | 4.2 | 5.0 | ... | 10.3 |
| ... | ... | ... | ... | ... | ... |
| ... | ... | ... | ... | ... | ... |
| $P_n$ | $T_n$ (Neutrophil) | 6.4 | 3.2 | | 20.5 |

In an exemplary embodiment, the data set may be separated into 3 subsets: training set, validation set and testing set. The training set may include training features from images that have been classified and coded by one or more human experts. This coding (called human reference coding) may be utilized to train the classifier (as a training dataset) and/or may be used as a validation dataset. After training the first level model 600, the training and validation features or data may be used to evaluate the performance of the CL first level model 600. The testing set may include images of uncharacterized cells and/or particles.

In an exemplary embodiment of the architecture model 650 illustrated in FIG. 6A, the data plays a key role because it defines the components of the architecture based on its complexity. In the exemplary embodiment illustrated in FIG. 6A, the architecture is composed of two levels of analysis components. In the first level model 600, a general classifier is trained to match the training data. In the second level model 640, specialized classifiers provide a second opinion for hard to classify samples 630 identified during the validation of the first level model.

First Level Model of the Classifier Architecture

In an exemplary embodiment, the first level (L1) model 600 of an architecture may be composed of a classifier model CL. The classifier CL may be any machine learning model capable of mapping a set of input features 610 to a known class label as defined by the training data set. Examples of machine learning models suitable for this architecture may be Random Forest, multiclass Support Vector Machines (SVMs), Feedforward Neural Networks (FNNs), etc.

In an exemplary embodiment, a Random Forest machine learning model may be selected to map the input feature vector into one of the blood cell category $C_j$, $1 \le j \le m$ defined in the training data set. In some instances, a Random Forest may be an ensemble classifier comprised of a multitude of decision trees that may each be trained on a different portion of the training set. The final classification decision of the Random Forest may be the mode of the classification decisions of the individual trees. The advantage of a random forest over a single decision tree classifier is that a Random Forest is less prone to over fitting on the training set because a Random Forest classification decision is an aggregate response of multiple independently trained decision trees. In some instances, the trees of the Random Forest machine may be trained using 80% of the data. In some instances, the Random Forest includes 64 trees.

Figure 6B:
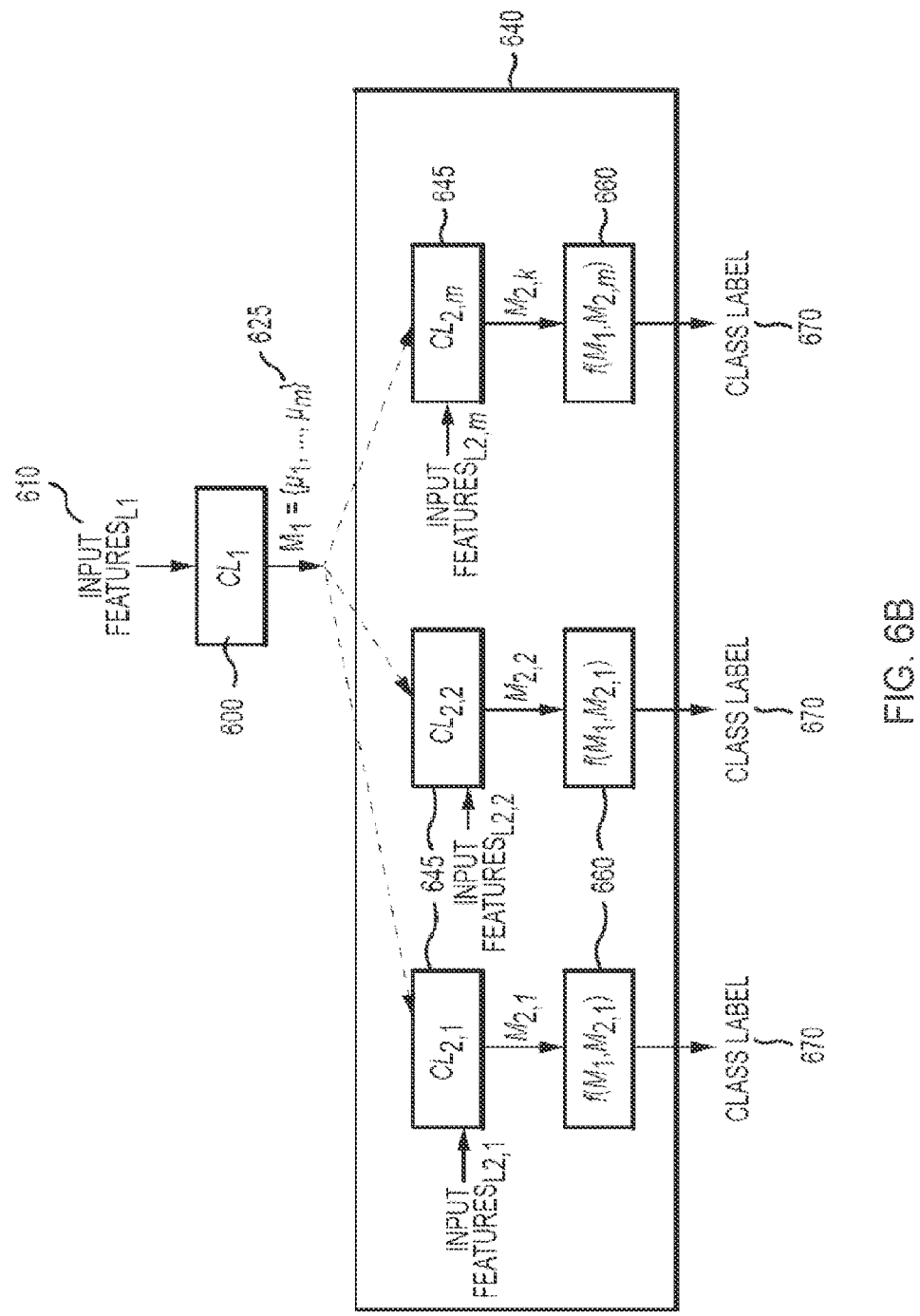

In some instances, the Random Forest may be trained using the bootstrap aggregating (bagging) technique FIG. 6B. Given a training set of cell images $P_i$ and corresponding target labels $T_i$, the bagging technique, for B iterations, repeatedly selects a random sample with replacement of the training set. The resulting B sample sets may be used to train B decision trees, forming the random forest CL. By sampling with replacement, some training samples may be repeated across the sample sets. This sampling strategy is known as bootstrap sampling and reduces the variance (i.e. susceptibility to over fitting) of the trained classifier, without increasing the bias. In some instances, the output of the CL is a set of scores $M=\{\mu_1, \mu_2, \ldots, \mu_j \ldots, \mu_m\}$ 625, one per category, where $\mu_j$ is a real number. Large values of $\mu_j$ indicate belongingness to a particular cell class. In this context, the higher the score $\mu_j$ the more likely the input feature 610 belongs to the cell category j and the less

16 the level one $M_i$ scores 625. The expectation is that $M_i$ scores 625 with a maximum $\mu_j$ close to 0.5 will be associated with a low probability of correct preliminary classification value in level one.

The following equation may be applied to calculate matrices of correct preliminary classification probability Pr for pairs of categories $\{C_j, C_k\}$:

Give a pair of categories $\{C_j, C_k\}$, $1 \le j \le m$, $1 \le k \le m$, $j \ne k$ The probability of correct classification may be computed as $$Pr_{\{C_j, C_k\}}(M) = \frac{\Sigma \, TPos_i}{\Sigma \, Pos_i}$$

Where $$TPos_i = \left\{ \begin{array}{l} 1 \; \text{if} \; (L_i = C_j \; \text{OR} \; L_i = C_k) \text{AND}(L_i = T_i) \\ 0 \; \text{if} \; (L_i = C_j \; \text{OR} \; L_i = C_k) \text{AND}(L_i \ne T_i) \end{array} \right\}$$

$$Pos_i = \left\{ \begin{array}{l} 1 \; \text{if} \; (L_i = C_j \; \text{OR} \; L_i = C_k) \\ 0 \; \text{otherwise} \end{array} \right\}$$

A minimum value for $\Sigma \, Pos_i$ may be adopted to avoid biasing of results at low $\Sigma \, Pos_i$ values. TABLE 2 provides an example of the calculation of $Pr_{\{C_j, C_k\}}$ for two cell categories (i.e., Neutrophils and Eosinophils) on a given training and validation data set. Assuming a subset of all positive Neutrophil and Eosinophil subset of data is available with corresponding predicted class label $L_i$, target label $T_i$ and M scores for that subset, matrices of $\Sigma \, TP os_i$ and $\Sigma \, Pos_i$ may be constructed to find $Pr_{\{Neutrophil, Eosinophil\}}$.

TABLE 2

| | | Eosinophil Score | | | | | | | | | | |
|---|---|---|---|---|---|---|---|---|---|---|---|---|
| | $\mu$ | 0 | 0.1 | 0.2 | 0.3 | 0.4 | 0.5 | 0.6 | 0.7 | 0.8 | 0.9 | 1 |
| Neutrophil | 0 | N/A | N/A | N/A | N/A | N/A | 100.0% | 100.0% | 100.0% | 100.0% | 100.0% | 100.0% |
| Score | 0.1 | N/A | N/A | N/A | 100.0% | 66.7% | 100.0% | 100.0% | 96.2% | 99.2% | 99.8% | 100.0% |
| | 0.2 | 100.0% | 66.7% | 50.0% | 66.7% | 74.2% | 81.9% | 94.9% | 97.9% | 96.3% | 100.0% | N/A |
| | 0.3 | 99.2% | 100.0% | 42.3% | 60.0% | 82.5% | 84.2% | 86.9% | 86.8% | N/A | N/A | N/A |
| | 0.4 | 98.8% | 85.1% | 71.0% | 47.1% | 55.0% | 71.3% | 93.1% | N/A | N/A | N/A | N/A |
| | 0.5 | 99.8% | 91.0% | 77.9% | 59.8% | 40.6% | 68.8% | N/A | N/A | N/A | N/A | N/A |
| | 0.6 | 99.8% | 94.1% | 78.9% | 64.7% | 65.0% | N/A | N/A | N/A | N/A | N/A | N/A |
| | 0.7 | 99.7% | 96.8% | 90.3% | 81.6% | N/A | N/A | N/A | N/A | N/A | N/A | N/A |
| | 0.8 | 99.9% | 96.5% | 93.9% | N/A | N/A | N/A | N/A | N/A | N/A | N/A | N/A |
| | 0.9 | 99.9% | 97.9% | N/A | N/A | N/A | N/A | N/A | N/A | N/A | N/A | N/A |
| | 1 | 100.0% | 100.0% | N/A | N/A | N/A | N/A | N/A | N/A | N/A | N/A | N/A | uncertainty there is about that assessment. Thus, a preliminary category label for the input feature 610 may initially be given by the category corresponding to the maximum value $\mu_j$ in M 625.

After training the first level model 600, both the training and validation data may be used to evaluate the performance of the CZ first level model 600. For a given input feature vector $F_i$, a predicted class label $L_i$ with corresponding M scores may be obtained for each input cell image $P_i$. This information may then be used as input to the design process of the second level model 640.

Second Level Model of the Classifier Architecture

The set of $M_i$ scores 625 may be analyzed to establish the probability of correct cell preliminary classification by the first level model 600. The probability of correct preliminary classification may be estimated by using the level one predicted class label $L_i$, the human expert target label $T_i$ and In the example of TABLE 2, cells producing M scores 625 when the probability is greater than or equal to 98%, the second level model 640 need not be used. Further, cells producing M scores 625 close to 0.5 may be less likely to generate a correct preliminary classification in the first level model. A Neutrophil score=0.5 and an Eosinophil score=0.4 provided by the level one CL classifier 600 produces the highest level of uncertainty in the decision with a sensitivity rate of 40.6%. Neutrophil and Eosinophil scores were rounded for binning purposes.

The probability matrices $Pr_{\{C_j, C_k\}}$ exemplified in TABLE 2 have at least two main purposes. First, the matrices may be used to establish an overall measurement of uncertainty for pairs of categories $\{C_j, C_k\}$. Second, cell images in the training and validation data set associated to low or high probability values in $Pr_{\{C_j, C_k\}}$ may be selected as candidates for training the second level component 640 of the cascade classifier architecture. To establish an overall measurement of uncertainty, it is possible to calculate the sum of all probability values on each $\Pr_{\{C_j,\ C_k\}}$. Pairs of categories having larger sum values will have less uncertainty associated to their discrimination. In more detail, for each category $C_j$, an ascending sorted list $D_{C_j}$ of $\Sigma\Pr_{\{C_j,\ C_k\}}$ values is created for $1 \le k \le m$, $j \ne k$. Categories at the top of the sorted list correspond to those having the lowest classification performance in relation to category $C_j$. In some cases, it is possible to have an empty list when a particular combination of pairs is easily discriminated and no classification errors are found in the training or validation data sets. An example of a sorted list $D_{C_j}$ is shown in TABLE 3.

TABLE 3

| $C_j$ | 1st | 2nd | 3rd |
|---|---|---|---|
| NEUT | PYKN | MONO | EOSN |
| LYMP | BASO | ATYP | MONO |
| MONO | LYMP | NEUT | ATYP |
| EOSN | NEUT | PYKN | LYMP |
| BASO | LYMP | | |
| BAND | NEUT | | |
| META | NEUT | MYLO | |

In the example of TABLE 3, the level one classifier generates higher rates of error when trying to discriminate between Neutrophils and Pyknotic (aged) cells and less preliminary classification errors against Monocytes or Eosinophils.

Using the information provided by $\Pr_{\{C_j,\ C_k\}}$ and $D_{C_j}$ it is possible to define the second level model 640. For each non-empty list $D_{C_j}$ a second level model 640 is created depending on data availability. Each specialized classifier is trained only with the data associated to low classification rates as defined in $\Pr_{\{C_j,\ C_k\}}$. Prior to training, a new feature selection process is carried out using the subset of training data selected. The features used in the second level model 640 may be different from the ones used in the first level model 600. Their complexity and computational cost in most cases may be higher in order to capture more details in the image. This increase in complexity is balanced by having a first level model 600 capable of handling the majority of cell and particle types and leaving the second level model 640 for the most problematic but rare cases. In practice, not all categories have a second level model 640 specialized classifier, as data available for those cases might not be sufficient or the performance of the second level model 640 might not improve the performance of the first level model 600.

After training is completed, the specialized second level model 640 may provide a second score $M_{2,k}$ that may be combined 660 with the first level model 600 preliminary classification scores 625 to provide a final class label 670. FIG. 6B shows the architecture of an exemplary cascade classifier.

In an exemplary architecture, each level two classifier may be composed of a classifier $CL_{2,j}$ 645 associated with the second level model 640 and a transfer function $f$ 660. The classifier $CL_{2,j}$ 645 may be any machine learning model capable of mapping a new set of input features to a known class label. Examples of machine learning models suitable under this architecture may be Support Vector Machines (SVMs), Feedforward Neural Networks (FNNs), Random Forest, etc. The classifier $CL_{2,j}$ 645 may be trained to assign the input feature vector into any of the $D_{C_j}$ cell categories. The output of $CL_{2,j}$ 645 may be determined by the value of the transfer function $f$ 660 on each classifier.

18

The transfer function $f$ 660 may serve the purpose of combining the M score 625 from the first level model 600, the $\Pr_{\{C_j,\ C_k\}}$ probability value and the $CL_{2,j}$ 645 output score. The function $f$ 660 may be designed to provide a continuous real value that takes into account classification scores from both the first level model 600 and the second level model 640. High values of function $f$ 660 may be interpreted as a confirmation of the preliminary category label j as the final class label 670. The following is an example of a transfer function between level one and level two classifiers:

$$f = \left(\Pr_{\{C_j,C_k\}}(M) \times \max(M_1)\right) + \left(\left(1 - \Pr_{\{C_j,C_k\}}(M)\right) \times \max(M_2)\right)$$

Figure 7:
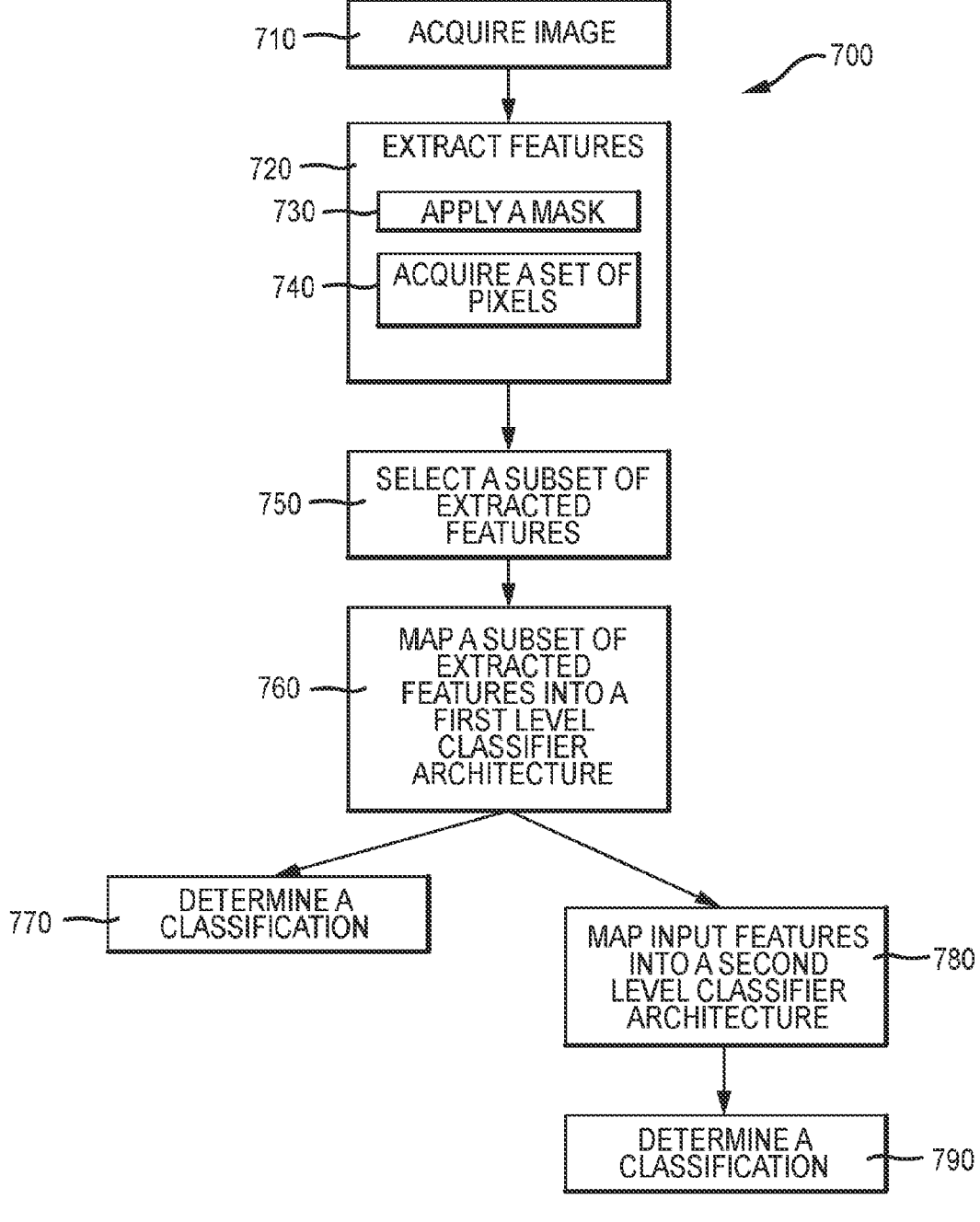
FIG. 7 is a flow chart illustrating one example of a method for determining a classification of a particle in a biological sample according in some embodiments of the invention.

To further illustrate the methods and systems of this disclosure, an example method as performed on system 100 is depicted graphically in FIG. 7. In FIG. 7, an image is acquired 710, a subset of extracted features 720 is selected 750 and mapped into a first level model architecture 760. The first level model architecture 760 may compare the probability value to a predetermined comparison table, determining a cell classification 770 if the probability value is at or above a threshold value, or use a second level model architecture 780 if the probability value is below the threshold value. The second level model architecture may combine create a sorted list of values according to a classification performance in relation to a blood cell category, combining the probability value and the sorted list to create a second level probability value, and using the first level probability value and the second level probability value to determine a cell classification 790.

The feature extraction 720 of FIG. 7 may be any of the methods described above in this disclosure, including those depicted in, or described with respect to, FIGS. 3-6. Similarly, the first 760 and second 780 level classifiers of FIG. 7 may be any of the classifiers described above in this disclosure, including those depicted in, or described with respect to, FIGS. 6A-6B.

In some cases, system and method embodiments of the present invention encompass particle image classification techniques such as those described elsewhere herein.

An advantage of the hierarchical or cascaded model of the present disclosure includes the benefit of limiting the analysis to a smaller subset of features. This may require less feature extraction and may allow for easier pinpointing of reasons for misclassification. In the present disclosure, solving the classification problem in terms of an architecture composed of low dimension (i.e., small number of input features) classifiers could potentially allow the visualization (i.e., plotting) of the interaction of the feature values in 2D or 3D plots, which in turns helps the classifier designer to better understand and comprehend the decision functions resulting from training algorithms, including but not limited to SVMs and FNNs. The two-step architecture of the system allows for more focused, faster processing and further allows the system to reserve processing resources for other operations.

Another advantage of the present disclosure is that architecture complexity may be better controlled. Architectural complexity may be introduced in early or later stages of the classification task. In most cases the majority of the features of the images will not need to be extracted or determined. In most cases, feature selection may be postponed until later within the cascaded architecture. To accurately solve a classification problem, a single complex classifier may have to include or use all of the discriminatory features in a single step or pass. The classifier model's subsequent combination and/or use of those features in the most optimal way may necessarily therefore be very complex, and may not be linear. In this approach, computationally cheap (also known as simple or inexpensive) features may be used to classify a large percentage of biological particles. In some cases, using a computationally cheap feature may be all that is required to classify a particle. If classification error exists for some biological particles, then more refined (also known as complex) features (which might not be actually useful for the "easier" large group) may be selected and extracted for those that the computationally cheap features are not able to identify. In general this may also allow for an easier to understand architecture. The model may also use common or shared features across classifiers to further reduce complexity.

Another advantage of the present disclosure is that the cascaded architecture of the classifier system is modular, scalable and simple to post-analyze. The output of the system may be traced back to individual classifiers. Individual classifiers may be retrained or upgraded while maintaining the rest of the architecture untouched. By having dedicated classification modules it is possible to retrain—one specific model at a time—as needed. For example, if new data related to a particular cell condition is collected (i.e., Pyknotic Neutrophils) then the Pyknotic Neutrophil-Eosinophil Level 2 classifier may be retrained without affecting other modules in the architecture.

Another advantage of the present disclosure is that the concept of transfer functions between the first and second level of the classifier allows a smooth transition between both levels. This reduces variability in the system response when similar images with small changes in feature values are processed due to the fact that there are no hard thresholds but rather a continuous transition between the two levels.

Further and Related Exemplary Embodiments

Blood particle images may be captured using a digital microscope camera and further analyzed for classification purposes. The assignment of blood particle images into different classes or categories can be a costly computational task. It can involve the extraction of numerical or categorical values known as features from the blood particle image. These features can have different degrees of computational complexity. Typically, color based features are fast to compute whereas texture and shape features are slow and can impose a constraint for real time classification. The real time analysis constraint can relate to the fact that the processing of a stream of blood cell particles often must conclude within a certain expected time in order for the acquisition system to meet predefined throughput requirements.

In many cases, blood cell particles can be accurately classified using low complexity information like color based features. However, under certain disease conditions or system related changes (stain, focus, cell aging, others) it may be useful to involve additional features with a higher complexity load to correctly identify the appropriate cell category. Computing and applying the high complexity features for all particles, however, may not be feasible due to time and computing constraints.

Embodiments of the present invention encompass classification architectures suitable for real time classification of blood particle images.

Blood cell recognition can be a complex task that involves segmentation, feature extraction, and classification phases which are executed in a time sensitive manner oftentimes on hardware with limited computational resources. It is therefore helpful when each phase in the system is efficient. The feature extraction component is typically the most impacted and often compromises between feature complexity and descriptive power versus computational efficiency.

Embodiments of the present invention employ a hierarchical classification model that leverages the use of more simplistic, efficient features for easier, more common classification events and more complex, expensive features for more difficult, rarer events. Relatedly, embodiments of the present invention involve the consideration of classification confidence and the probabilities of event difficulty, which can improve computational efficiency.

Embodiments of the present invention provide modularity which expands the ability to troubleshoot and investigate potential misclassifications and shortcomings of the trained classifiers. Embodiments of the present invention also enable the developer to visualize the input feature space and discern the reason behind a potential misclassification. Cascaded models such as the architecture disclosed here, have the advantage of modularizing the classification problem into an ensemble of classifiers with lower dimensional, visually amenable input feature spaces. With such models pinpointing reasons for misclassification can easily be performed.

Another advantage of the modularity of the present disclosure is that each lower-dimensional classifier in the ensemble can be less complex. For instance, when employing a single high-dimensional classifier, each cell image is typically processed by the classifier across all input dimensions to yield a class label. In a cascaded model, a cell image is processed by only a subset of the ensemble and each classifier has a relatively lower input dimensionality resulting in fewer computational operations per image. Furthermore, feature computation can be postponed until a cell event reaches a particular classifier within the cascade that requires the specific feature. In most cases the majority of the features will not need to be computed. The model can also leverage shared features across classifiers further reducing complexity.

In some embodiments, this disclosure provides for a classification architecture suitable for real time classification of blood particle images. A typical image based classification can be composed of four main steps: Image acquisition, feature extraction, feature selection and classifier architecture. Throughout this disclosure, the technical description is often focused on the feature selection and classifier architecture. In some cases it is assumed that an image acquisition is in place to capture the blood particle images. It may also be assumed, that a pool of features with different degrees of discriminatory power and levels of computational complexity are available for designing and training the individual classifiers within the proposed architecture. Features can be directly obtained from the image or be a byproduct of additional dimensionality reduction techniques such as Principal Component Analysis.

Feature selection can be understood in this context as the process of choosing from a large pool of features the ones providing the greatest discrimination power between one or more blood particles. In a traditional image based classification system, feature selection and classifier architecture design are commonly two independent processes. Features are selected based on a predefined performance criteria and a classifier architecture is designed and trained with the selected features. In embodiments of the present invention, however, the feature selection process and architecture can be closely coupled. The feature selection process can guide the classifier architecture design. FIG. 8 depicts aspects of blood particle images, blood particle categories, and extracted features according to embodiments of the present invention.

In one simple form, the feature selection process can be conducted on a feature by feature basis in the following way. In a more complex form, combination of two or more features can be chosen to evaluate their discrimination power. If a combination of features are evaluated, then the classifier method that will ultimately use those features can be trained and its output used for the purposes of computing the chosen discriminatory coefficient.

---

For blood category $C_j$, $1 \le j \le m$
    Define $G_j$ as the subset of images $P_i$, with label $T_i$, $1 \le i \le n$ matching blood category $C_j$
    For all features $F_s$, $1 \le s \le m$
        Compute discriminatory coefficient $D_{s,j}$ of feature $F_s$ between $G_j$ and the rest of the particle images in the data set.
        The coefficient $D_s$ can be computed by a variety of methods such as Area Under the Curve (AUC) of the Receiver Operating Curve (ROC), information entropy or other available method.
    End
End

---

The category $C_j$ with the highest $D_{s,j}$ is logged into a separate list as the label for classifier $Cl_j$, $1 \le j \le m$, starting at $j=1$, and removed from analysis to reduce complexity in the discrimination of the categories remaining. The category label $Cl_1$ eventually will become the first classifier in the proposed architecture, while $Cl_m$ will be the last one. The process described above is repeated until all categories $C_j$ have been analyzed and make it to the $Cl_j$ set.

In general terms, one embodiment of the disclosed method allows a ranking of each category $C_j$ in terms of its separability from the rest of the categories. This sorted list is used to define the architecture scaffold of the classifier. Categories with highest level of separability (i.e., easier to classify from the rest) will be the assessed first by the classifier architecture. The discriminatory coefficients $D_{s,j}$ and complexity indexes $O_s$ are stored for further classifier feature assignment.

Figure 9:
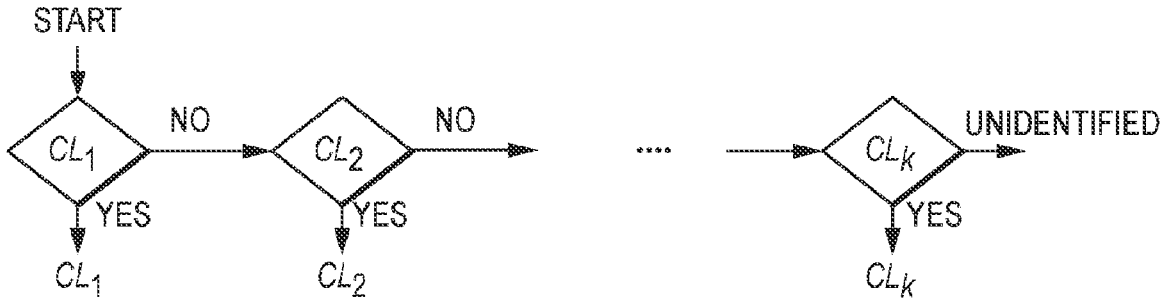
FIG. 9 illustrates a cascade model classifier architecture according to some embodiments of the Invention.

In one embodiment, the classifier architecture may follow a cascade model as shown in FIG. 9. Given an input image, the classifier $Cl_1$ attempts to identify if the image belongs to its associated category. If the output of classifier $Cl_1$ favors that category the input image is classified as $Cl_1$ and the classification ends. Otherwise, the image is passed to $Cl_2$ and so on until all classifiers are exhausted.

Figure 10:
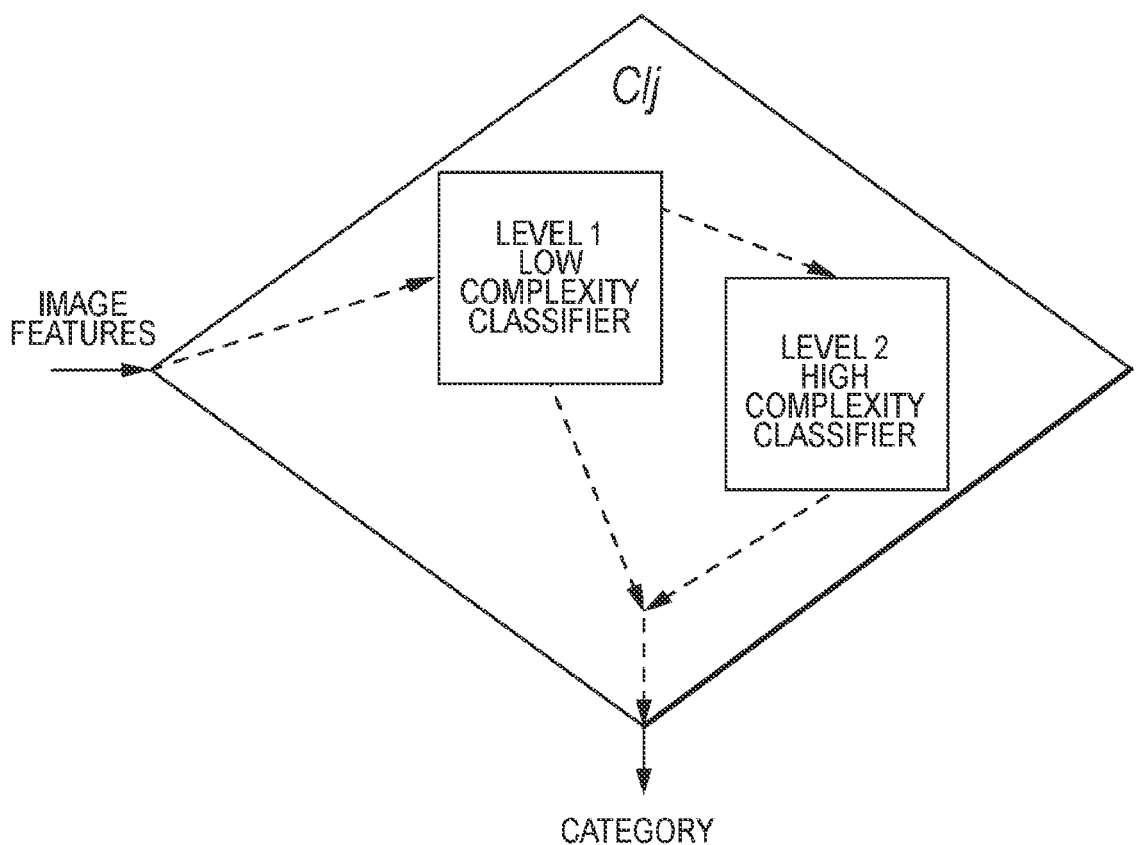
FIG. 10 illustrates a proposed internal structure for a classifier Cij according to embodiments of the present invention.

The internal structure of each classifier $Cl_j$ is unique because it provides a balance between complexity and performance. This approach has not been seen on other alternatives approaches. FIG. 10 depicts a proposed internal structure for classifier $Cl_j$ according to embodiments of the present invention. In one embodiment, the classifier $Cl_j$ is composed of two classifiers. The first one known as Level 1 classifier, is commonly a simple linear classifier model that uses a reduced number of features (usually three or less to allow easy visualization of the feature space). The feature selection for this Level 1 classifier is given by a weighted combination of the $D_{s,j}$ feature discriminatory coefficient obtained above and the level of computational complexity $O_s$ associated to each feature. Uncorrelated features with high discriminatory coefficient and low computational complexity are ideal candidates for Level 1. Machine learning classifier models such as Support Vector Machines, Percep-tron or other simple models can be used to automatically train the Level 1 classifier.

In one embodiment, the Level 2 classifier is a more complex classifier model. Commonly, based on a non-linear model with a complex structure to handle non-obvious relationships among the features. The feature selection for this Level 2 classifier is also given by a weighted combination of the $D_{s,j}$ feature discriminatory coefficients obtained above and the level of computational complexity $O_s$ associated to each feature. Features with high discriminatory coefficient and high computational complexity are ideal candidates for Level 2. The number of features commonly goes above three thus visualization of the feature space is no longer possible. Machine learning classifier models such as Multilayer Feedforward Neural Networks, Bootstrap, or any other complex models can be used to automatically estimate the model parameters.

In one embodiment of the proposed architecture, the Level 1 classifier handles the vast majority of input images, thus lowering computational time and simplifying analysis of the classification flow. The Level 2 classifier engages only when the Level 1 classifier decision is uncertain and not trustable. The following approach is proposed to assess the uncertainty of the Level 1 classifier and control the contri-bution of Level 1 and Level 2 classifier to the final outcome of $Cl_j$.

Figure 11:
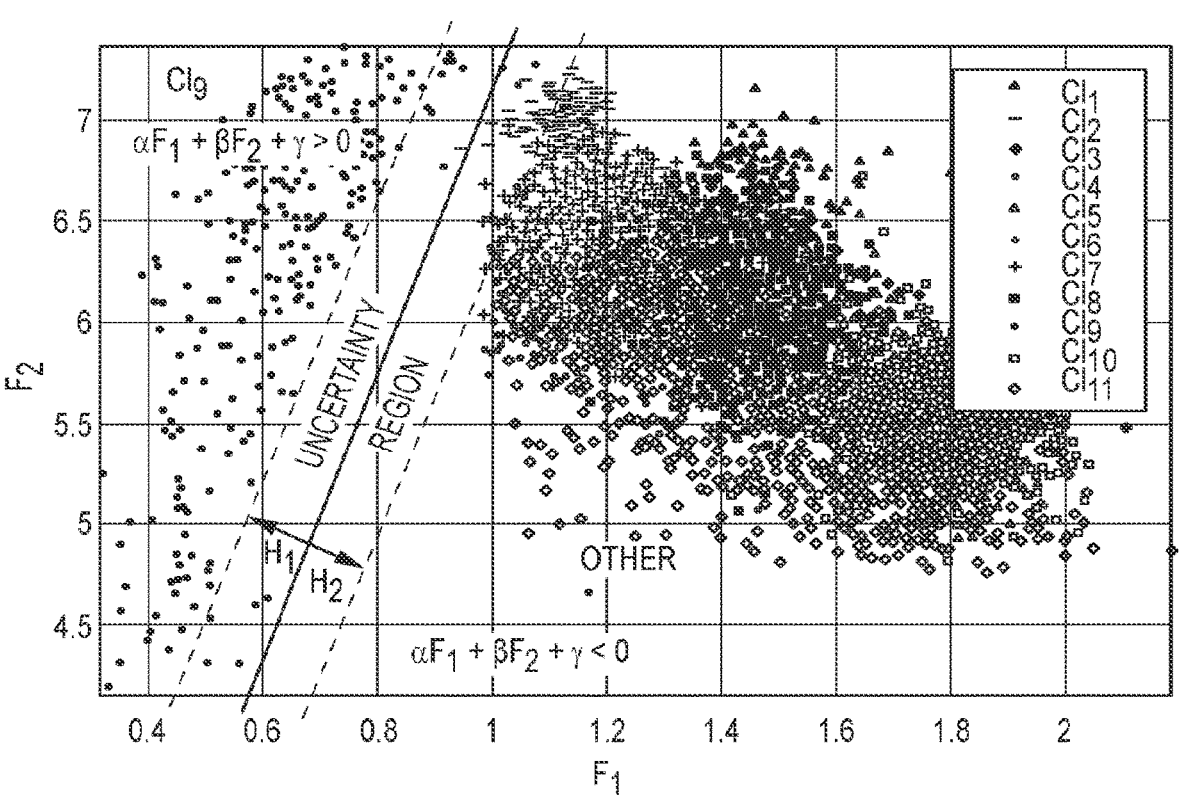
FIG. 11 illustrates an exemplary Level 1 classifier given two features $F_1$ and $F_2$ according in embodiments of the present invention.

In one example, two given features $F_1$ and $F_2$ are used as input to a Level 1 classifier in charge of identifying category $Cl_9$ as shown in FIG. 11. The Level 1 classifier model output $\varphi_{Level_1}$ is defined as the linear combination of features $F_1$ and $F_2$ with model coefficients $\alpha$, $\beta$ and the bias term $\gamma$. A larger number of model coefficients will be present as the number of input features increases. The model coefficients can be obtained by a machine learning algorithm such as linear discriminant analysis, support vector machine or any other suitable approach.

A linear combination value equal to zero (i.e., $\varphi_{Level_1}=0$) corresponds to the exact location of the boundary separating $Cl_9$ from the rest of the blood particles categories (i.e., "other"). The linear combination value $\varphi_{Level_1}$ increases or decreases proportional to the perpendicular distance to $\varphi_{Level_1}=0$. Blood particles in $Cl_9$ close to the upper left corner of the figure will have larger positive $\varphi_{Level_1}$ values than those close to the boundary. On the other hand, blood particles in the "other" region close to the lower right corner of the figure will have large negative $\varphi_{Level_1}$ values.

As mentioned above, the line defined by $\varphi_{Level_1}=0$ corre-sponds to the boundary separating $Cl_9$ from the rest of the blood particles categories but in addition, it corresponds to the points where the uncertainty about the classifier decision is at its highest level. A small change in features $F_1$ and $F_2$ values can change the classifier decision one way or another around this area. Using the Level 1 classifier model, feature values $F_1$ and $F_2$ and corresponding target label $T_i$, $1 \le i \le n$, it is possible to define an uncertainty region around boundary $\varphi_{Level_1}=0$ to identify value combinations of features $F_1$ and $F_2$ that will yield a highly uncertain response from the classifier.

In this example, the uncertainty region can be defined by setting offsets $H_{Level_1}{}^1$ and $H_{Level_1}{}^2$ ever, around the boundary. In the simplest implementation, the offsets could have the same value. The actual values of offsets can be defined by setting an arbitrarily performance metric for the Level 1 classifier. For example, it might be desired to have a high degree of specificity in the non-uncertain regions, which means that if a blood particle is detected outside the uncertainty region there is a high confidence that the blood particle will be correctly classified.

In one embodiment, the Level 2 classifier will only be called and its corresponding input features (commonly different from Level 1 features) computed when a particular combination of features (in the example $F_1$ and $F_2$) for a blood particle fall inside the Level 1 uncertainty region. This unique design allow the overall classification system to remain simple and fast for easy to classify blood particles but flexible enough to handle more complex scenarios when needed.

In one embodiment, the same approach to create the Level 2 uncertainty region can be applied to the Level 2 classifier to define its offsets. Once offsets $H_{Level_2}{}^1$ and $H_{Level_2}{}^2$ are determined, a couple of transition functions $\eta_{Level_1}(\varphi_{Level_1})$ and $\eta_{Level_2}(\varphi_{Level_2})$ where $-1\leq\eta_{Level_1}(\varphi_{Level_1})\leq1$ and $-1\leq\eta_{Level_2}(\varphi_{Level_2})\leq1$ can be defined as depicted in FIG. 12. This set of functions allow a smooth transition between Level 1 and Level 2 classifier outputs by linearly combining their response according to each classifier's uncertainty value. Note that function $\eta_{Level_2}$ commonly have a non-linear behavior in the uncertainty region due to the complex nature of the Level 2 classifier. The following equation describes how the final classifier $Cl_j$ output is produced:

$$Cl_j \; \text{Classifier Response} = \eta_{Level_1}\left(\varphi_{Level_1}\right) + \eta_{Level_2}\left(\varphi_{Level_2}\right)$$

The following workflow summarizes the processing of a single image $P_i$ by the proposed classifier architecture for real time processing (recall phase):

Given an input image $P_i$

For all classifiers $Cl_j$

Analyze image $P_i$ to extract features F needed for $Cl_j$ Level 1 classifier

Input features F into Level 1 classifier to compute $\varphi_{Level_1}$ (Level 1 output)

If $\varphi_{Level_1} \geq H_{Level_1}{}^2$ then classify input image $P_i$ as blood particle category $Cl_j$ and finish classification task of input image $P_i$ If $\varphi_{Level_1} \leq H_{Level_1}{}^1$ then classify input image $P_i$ as blood particle category "other" and continue to classifier $Cl_{j+1}$ If $H_{Level_1}{}^1 < \varphi_{Level_1} < H_{Level_1}{}^2$ then Compute transition function $\eta_{Level_1}(\varphi_{Level_1})$ for Level 1 classifier Analyze image $P_i$ to extract features F needed for $Cl_j$ Level 2 classifier Input features F into Level 2 classifier to compute compute $\varphi_{Level_2}$ (Level 2 output)

If $(\varphi_{Level_2} \geq H_{Level_2}{}^2$ then classify input image $P_i$ as blood particle category $Cl_j$ and finish classification task of input image $P_i$ If $(\varphi_{Level_1} \leq H_{Level_2}{}^1$ then classify input image $P_i$ as blood particle category "other" and continue to classifier $Cl_{j+1}$ If $H_{Level_2}{}^1 < \varphi_{Level_2} < H_{Level_2}{}^2$ then Compute transition function $\eta_{Level_2}(\varphi_{Level_2})$ for Level 2 classifier Compute final $Cl_j$ Classifier Response using a linear combination of $\eta_{Level_1}$ and $\eta_{Level_2}$ as indicated above If $Cl_j$ Classifier Response > 0 then classify input image $P_i$ as blood particle category $Cl_j$ and finish classification task of input image $P_i$ If $Cl_j$ Classifier Response < 0 then classify input image $P_i$ as category "other" and continue to classifier $Cl_{j+1}$.

End

End

End

If input image $P_i$ was not classified by any of the $Cl_j$ classifiers then label image $P_i$ as unidentified.

All features of the described methods are applicable to the described systems mutatis mutandis, and vice versa.

The examples presented herein are intended to illustrate potential and specific implementations of the invention. It may be appreciated that the examples are intended primarily for purposes of illustration for those skilled in the art. There may be variations to these diagrams or the operations described herein without departing from the spirit of the invention. For instance, in certain cases, method steps or operations may be performed or executed in differing order, or operations may be added, deleted or modified.

All patents, patent publications, patent applications, journal articles, books, technical references, and the like discussed in the instant disclosure are incorporated herein by reference in their entirety for all purposes.

It is to be understood that the figures and descriptions of the disclosure have been simplified to illustrate elements that are relevant for a clear understanding of the disclosure. It should be appreciated that the figures are presented for illustrative purposes and not as construction drawings. Omitted details and modifications or alternative embodiments are within the purview of persons of ordinary skill in the art. Furthermore, in certain aspects of the disclosure, a single component may be replaced by multiple components, and multiple components may be replaced by a single component, to provide an element or structure or to perform a given function or functions. Except where such substitution would not be operative to practice certain embodiments, such substitution is considered within the scope of the disclosure.

Different arrangements of the components depicted in the drawings or described above, as well as components and steps not shown or described are possible. Similarly, some features and sub-combinations are useful and may be employed without reference to other features and sub-combinations. Aspects and embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

While exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A method of determining a classification of a particle in a biological sample comprising:
   acquiring an image of the particle with a digital camera;
   receiving the image of the particle at a processor system; and
   utilizing the processor system to execute computer executable code stored on a non-transitory computer readable medium, the computer executable code comprising instructions that, when executed on the processor system, cause the processor system to:
      input a first set of features into a first classifier, the first classifier configured to provide a first label among a set of labels and a first probability value associated with the first label, and
      input a second set of features into a second classifier if the first probability value is below a first threshold, the second classifier configured to provide a second label among the set of labels.

2. The method of claim 1, wherein the second label is utilized if the second label is at or above a second threshold.

3. The method of claim 2, wherein the first and second thresholds are different numerical amounts.

4. The method of claim 1, wherein inputting the first set of features into a first classifier comprises applying a first mask to the image.

5. The method of claim 4, wherein inputting the first set of features into a second classifier comprises applying a second mask to the image.

6. The method of claim 5, wherein the first mask and the second mask are circular or ring-shaped.

7. The method of claim 5, wherein an application of each mask reveals different pixels concentrically outside a center of the image.

8. The method of claim 7, further comprising clustering a first set of pixels into a group, creating a color palette from the clustered group of pixels, determining a label for the image based in part on the color palette, or any combination thereof.

9. The method of claim 4, further comprising normalizing the image to a size of the first mask.

10. The method of claim 1, wherein the first set of features and the second set of features comprise different sets of features.

11. A method of determining a classification of a particle in a biological sample comprising:
   acquiring an image of the particle with a digital camera;
   receiving the image of the particle at a processor system;
   utilizing the processor system to execute computer executable code stored on a non-transitory computer readable medium, the computer executable code comprising instructions that, when executed on the processor system, cause the processor system to:
      input a first set of features into a first classifier, the first classifier configured to provide a first label among a set of labels and a first probability value associated with the first label, and
      input a second set of features into a second classifier, the second classifier configured to provide a second label, and
      apply the first label if the first probability value is at or above a first threshold, and apply the second label if the second label is at or above a second threshold among the set of labels.

12. The method of claim 11, wherein the first and second thresholds are different numerical amounts.

13. The method of claim 11, wherein inputting the first set of features into a first classifier comprises applying a first mask to the image.

14. The method of claim 13, further comprising normalizing the first mask to a unit magnitude, using a chosen color space, including red-green-blue (RGB) hue-saturation-value (HSV), hue-saturation-lightness (HSL), or hue-saturation-brightness (HSB), or any combination thereof.

15. The method of claim 13, wherein inputting the first set of features into a second classifier comprises applying a second mask to the image.

16. The method of claim 15, wherein the first mask and the second mask are circular or ring-shaped.

17. The method of claim 15, wherein an application of each mask reveals different pixels concentrically outside a center of the image.

18. The method of claim 13, further comprising normalizing the image to a size of the first mask.

19. The method of claim 18, further comprising clustering a first set of pixels into a group, creating a color palette from the clustered group of pixels, determining a label for the image based in part on the color palette, or any combination thereof.

20. The method of claim 11, wherein the first set of features and the second set of features comprise different sets of features.

\* \* \* \* \*